(12) United States Patent
Irisawa

(10) Patent No.: US 10,980,425 B2
(45) Date of Patent: Apr. 20, 2021

(54) ACOUSTIC WAVE DETECTION PROBE AND PHOTOACOUSTIC MEASUREMENT APPARATUS PROVIDED WITH THE SAME

(71) Applicant: FUJIFILM Corporation, Tokyo (JP)

(72) Inventor: Kaku Irisawa, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 444 days.

(21) Appl. No.: 16/102,438

(22) Filed: Aug. 13, 2018

(65) Prior Publication Data

US 2019/0000323 A1    Jan. 3, 2019

Related U.S. Application Data

(63) Continuation of application No. 15/410,583, filed on Jan. 19, 2017, now Pat. No. 10,070,792, which is a
(Continued)

(30) Foreign Application Priority Data

Feb. 29, 2012  (JP) .................................. 2012-043595
Feb. 22, 2013  (JP) .................................. 2013-033053

(51) Int. Cl.
*A61B 5/00*     (2006.01)
*G01N 29/24*   (2006.01)
*A61B 90/30*   (2016.01)

(52) U.S. Cl.
CPC .......... *A61B 5/0097* (2013.01); *A61B 5/0095* (2013.01); *A61B 90/30* (2016.02);
(Continued)

(58) Field of Classification Search
CPC ..... A61B 5/0097; A61B 90/30; A61B 5/0095; A61B 2090/306; A61B 2576/00;
(Continued)

(56) References Cited

U.S. PATENT DOCUMENTS 5,172,189 A    12/1992  Mitome
5,536,236 A    7/1996   Yabe et al.
(Continued)

FOREIGN PATENT DOCUMENTS

CN    101301222 A    11/2008
CN    101191970 B    6/2010
(Continued)

OTHER PUBLICATIONS

Chinese Office Action and Search Report for Chinese Application No. 201610816256.9, dated Nov. 4, 2019, with a partial English translation thereof.
(Continued)

*Primary Examiner* — Hien N Nguyen
(74) *Attorney, Agent, or Firm* — Birch, Stewart, Kolasch & Birch, LLP

(57) ABSTRACT

In an acoustic wave detection probe provided with a light guide section that guides measuring light such that the measuring light is outputted toward a subject and an acoustic wave transducer that detects a photoacoustic wave generated in the subject by the projection of the measuring light, the light guide section includes a homogenizer that flat-tops an energy profile of the measuring light entered from the upstream side of the optical system, a light condensing member that condenses the measuring light transmitted through the homogenizer, and a bundle fiber which includes a plurality of optical fibers and is disposed such that the measuring light transmitted through the light condensing member enters from an entrance end of the bundle fiber.

15 Claims, 13 Drawing Sheets

Related U.S. Application Data continuation of application No. 15/015,514, filed on Feb. 4, 2016, now Pat. No. 9,579,027, which is a continuation of application No. 14/456,568, filed on Aug. 11, 2014, now Pat. No. 9,282,900, which is a continuation of application No. PCT/JP2013/001182, filed on Feb. 27, 2013.

(52) U.S. Cl.
CPC ..... *G01N 29/2418* (2013.01); *G01N 29/2462* (2013.01); *A61B 2090/306* (2016.02); *A61B 2576/00* (2013.01); *G01N 2291/02466* (2013.01)

(58) Field of Classification Search
CPC ........... G01N 29/2462; G01N 29/2418; G01N 2291/02466; G02B 27/0927
See application file for complete search history.

(56) References Cited

U.S. PATENT DOCUMENTS

| | | | |
|---|---|---|---|
| 5,765,934 | A | 6/1998 | Okamori et al. |
| 2003/0023152 | A1 | 1/2003 | Abbink et al. |
| 2003/0145630 | A1 | 8/2003 | Hirano et al. |
| 2006/0184162 | A1 | 8/2006 | Smith |
| 2008/0279330 | A1 | 11/2008 | Ueki |
| 2009/0092358 | A1 | 4/2009 | Watanabe et al. |
| 2011/0314921 | A1 | 12/2011 | Tsujita |
| 2013/0190591 | A1 | 7/2013 | Hirson et al. |

FOREIGN PATENT DOCUMENTS

| | | | |
|---|---|---|---|
| CN | 102293667 | A | 12/2011 |
| JP | 1-218441 | A | 8/1989 |
| JP | 3-141316 | A | 6/1991 |
| JP | 9-106705 | A | 4/1997 |
| JP | 2001-337251 | A | 12/2001 |
| JP | 2004-193267 | A | 7/2004 |
| JP | 2005-43139 | A | 2/2005 |
| JP | 2005-302827 | A | 10/2005 |
| JP | 2006-18114 | A | 1/2006 |
| JP | 2006-84932 | A | 3/2006 |
| JP | 2006-122063 | A | 5/2006 |
| JP | 2007-293298 | A | 11/2007 |
| JP | 2008-116209 | A | 5/2008 |
| JP | 2010-12295 | A | 1/2010 |
| JP | 2012-5623 | A | 1/2012 |
| WO | WO 2010/018680 | A1 | 2/2010 |
| WO | WO 2011/137385 | A1 | 11/2011 |

OTHER PUBLICATIONS

Chinese Office Action dated Jul. 22, 2015 for Chinese Patent Application No. 201380011865.1.
International Search Report issued in PCT/JP2013/001182, dated Jul. 16, 2013.
Japanese Office Action dated Apr. 7, 2015, issued in corresponding Japanese Patent Application No. 2013-033053, with English translation.
Written Opinion of the International Searching Authority issued in PCT/JP2013/001182, dated Jul. 16, 2013.
Chinese Office Action and English translation thereof, dated Feb. 22, 2016 for Application No. 201380011865.1.
Decision to Grant a Patent issued in Japanese Application No. 2013-03053 with English Translation.
Notice of Allowance in U.S. Appl. No. 14/456,568, dated Nov. 6, 2015.
Notice of Allowance issued in U.S. Appl. No. 15/015,514, dated Oct. 17, 2016.
Notice of Allowance issued in U.S. Appl. No. 15/410,583, dated May 11, 2018.
Notice of Grounds for Rejection issued in Japanese Applicaiton No. 2013-033053 with English Translation.
Office Action issued in U.S. Appl. No. 14/456,568, dated Jun. 8, 2015.
Office Action issued in U.S. Appl. No. 15/015,514, dated Jun. 3, 2016.

a    b

DIFFUSION ANGLE OF LIGHT SHAPING DIFFUSER (deg.)

US 10,980,425 B2

ACOUSTIC WAVE DETECTION PROBE AND PHOTOACOUSTIC MEASUREMENT APPARATUS PROVIDED WITH THE SAME

CROSS-REFERENCE TO RELATED APPLICATIONS

This application is a Continuation of co-pending U.S. application Ser. No. 15/410,583, filed Jan. 19, 2017, which is a Continuation of U.S. application Ser. No. 15/015,514 filed on Feb. 4, 2016 (now U.S. Pat. No. 9,579,027), which is a Continuation of U.S. application Ser. No. 14/456,568 filed on Aug. 11, 2014 (now U.S. Pat. No. 9,282,900), which is a Continuation of PCT International Application No. PCT/JP2013/001182 filed on Feb. 27, 2013, which claims priority under 35 U.S.C. § 119 (a) to Japanese Patent Application No. 2012-043595 filed on Feb. 29, 2012 and Japanese Patent Application No. 2013-033053 filed on Feb. 22, 2013, the contents each of which are hereby expressly incorporated herein by reference in their entirety.

TECHNICAL FIELD

The present invention relates to a probe to be applied to a measurement target to detect an acoustic wave, and a photoacoustic measurement apparatus.

BACKGROUND ART

The photoacoustic spectroscopy is a method in which a pulsed light having a predetermined wavelength (e.g., wavelength range of visible light, near infrared light, or mid-infrared light) is projected onto a subject and a photoacoustic wave, which is an elastic wave generated as a result of absorption of the energy of the pulsed light by a specific substance in the subject, is detected, thereby quantitatively measuring the concentration of the specific substance (e.g., Japanese Unexamined Patent Publication No. 2010-012295). For example, the specific substance in the subject may be glucose, hemoglobin, or the like included in the blood. The technology that detects a photoacoustic wave in the manner described above and generates a photoacoustic image based on the detected signal is called photoacoustic imaging (PAI) or photoacoustic tomography (PAT).

There has conventionally been a problem described herein below in the measurements using the photoacoustic spectroscopy described above (photoacoustic measurements). That is, the intensity of the light projected onto the subject is significantly attenuated due to absorption and scattering in the process of traveling through the subject. The intensity of a photoacoustic wave generated in the subject based on the projected light is also attenuated due to absorption and scattering in the process of propagating through the subject. Consequently, it is difficult to obtain information of a deep portion of the subject by the photoacoustic measurements. In order to solve this problem, it is conceivable that, for example, the magnitude of generated photoacoustic wave is increased by increasing the amount of light energy projected into the subject through the use of high energy light.

In the case where high energy (1 mJ or more) light required in photoacoustic measurements is guided by an optical fiber, it is highly likely that the end face of the optical fiber is damaged and a durability problem of the optical fiber may possibly occur. Generally, when light is inputted to an optical fiber, the end face of the optical fiber is placed adjacent to the focal position of the condenser lens so that the beam diameter of the light fits into the core diameter of the optical fiber. Here, when the light is condensed by the condenser lens, however, the light is focused too narrowly and the energy is locally concentrated, whereby end face damage of the optical fiber may progress from the energy concentrated point as the origin.

In the meantime, for example, Japanese Unexamined Patent Publication No. 2004-193267 discloses that transmission of high energy light is realized by the use of a bundle fiber whose entrance end is fusion processed (fused bundle fiber) to efficiently reduce the light energy incident on a unit area.

DISCLOSURE OF THE INVENTION

The use of the method described in Japanese Unexamined Patent Publication No. 2004-193267 in the photoacoustic measurements, however, poses a problem that the homogeneity of the energy profile of the light outputted from the fused bundle fiber cannot be ensured. This is because the homogeneity of energy profile of light when entering the fused bundle fiber is not ensured by the method described in Japanese Unexamined Patent Publication No. 2004-193267. Although, it is described in paragraph 0017 of Japanese Unexamined Patent Publication No. 2004-193267 that the light is directed onto the fused bundle fiber as a spot with a diameter identical to that of the fused bundle fiber, the light is only focused by a lens against the entrance end of the fused bundle fiber in Japanese Unexamined Patent Publication No. 2004-193267. In this case, the energy profile of light when entering the fused bundle fiber is thought to have the Gaussian distribution as in normal light energy profiles. Then, it is presumed that there is an imbalance in the amount of energy of light traveling through each optical fiber of the bundle fiber.

In Japanese Unexamined Patent Publication No. 2004-193267, all that is required is to simply transmit light, so that it is not necessary to ensure the homogeneity of the energy profile of exiting light. In the photoacoustic measurements, however, the homogeneity of the energy profile of the light actually projected to the subject is required from the viewpoint of reconstructing quality photoacoustic signals, in addition to the transmission of high energy light. For that purpose, it is important to eliminate the imbalance in the amount of energy between each light traveling through each optical fiber of the bundle fiber.

The present invention has been developed in response to the aforementioned requirement, and it is an object of the present invention to provide an acoustic wave detection probe and photoacoustic measurement apparatus capable of transmitting high energy light and eliminating imbalance in the amount of energy between each light traveling through each of a plurality of optical fibers in photoacoustic measurements.

In order to solve the aforementioned problem, a photoacoustic wave detection prove of the present invention is a probe provided with a light guide section that guides measuring light such that the measuring light is outputted toward a subject and an acoustic wave transducer that detects a photoacoustic wave generated in the subject by the projection of the measuring light, wherein the light guide section includes:

a homogenizer that flat-tops an energy profile of the measuring light entered the light guide section;

a light condensing member that condenses the measuring light transmitted through the homogenizer; and a bundle fiber which includes a plurality of optical fibers and is disposed such that the measuring light transmitted through the light condensing member enters from an entrance end of the bundle fiber.

That is, in the present invention, the measuring light is passed through the homogenizer once to flat-top the energy profile and the beam diameter of the measuring light when entering the bundle fiber is controlled by the light condensing member.

In the probe according to the present invention, it is preferably that the homogenizer further diffuses the measuring light. In this case, it is preferable that the light condensing member condenses the measuring light such that a minimum beam diameter D defined by Formula 1 below satisfies Formula 2 below in relation to a diameter d of the bundle fiber, and the bundle fiber is disposed such that the measuring light enters the bundle fiber with the beam diameter D being 0.8 d to 1.2 d.

$$D = 2.5 \cdot f \cdot \tan\left(\sqrt{\left(\frac{\phi}{2}\right)^2 + \left(\frac{\theta}{2}\right)^2}\right) \quad \text{Formula 1}$$

$$0.8d \leq D \leq 1.2d \quad \text{Formula 2}$$

As used herein, f represents the focal length of the light condensing member; φ represents the spread angle of the measuring light when entering the homogenizer; and θ represents the diffusion angle of the homogenizer. The term "diameter of the bundle fiber" refers to a maximum distance between circumferences of the cores of farthest optical fibers among the plurality of optical fibers in the bundle fiber. The term "spread angle" refers to an angle by which the beam diameter of the laser light spreads in connection with the propagation. The term "diffusion angle" of the homogenizer refers to a design angle of diffusion, i.e., an angle by which the beam diameter of the laser light entered as parallel light and transmitted through the homogenizer spreads in connection with the propagation. The "spread angle" and the "diffusion angle" are expressed in full-width of plane angle. When measuring these angles, it is preferable that the beam diameters are measured at ten points or so within the range of propagation distance in which a given beam diameter spreads twice as large as the given diameter, and the angle is obtained from the slope of change in the beam diameter.

The term "beam diameter" refers to the diameter of a circle centered on the beam center (normally, position where the beam intensity is maximum) in which about 86.5% of the energy profile of laser light is included, i.e., the so-called $1/e^2$ diameter. In this case, if it is difficult to obtain the beam center due to an irregular distribution of beam intensity or the like, circles in which energy becomes 86.5% may be drawn exhaustively near the position presumed to be the beam center and the diameter of a circle having the minimum area among them may be used as the beam diameter.

In the probe according to the present invention, it is preferable that the light guide section includes a beam expander optical system immediately before the entrance side of the homogenizer, the beam expander optical system having an expansion factor that conforms to angular apertures of the plurality of optical fibers so that the measuring light is expanded to a beam diameter that conforms to the angular apertures of the plurality of optical fibers.

Further, in the probe according to the present invention, it is preferable that the entrance end of the bundle fiber is fusion processed.

Still further, in the probe according to the present invention, it is preferable that the outer circumferences of the plurality of optical fibers are covered with a material having high durability against optical energy at the entrance end. In this case, it is preferably that the material having high durability against optical energy is silica.

Further, in the probe according to the present invention, it is preferable that exit ends of optical fibers in each of a plurality of divided areas divided in an end face arrangement of the entrance end are disposed according to a relative magnitude with respect to each divided area to which the exit ends belong such that an energy profile when the measuring light exits from the exit ends of all optical fibers becomes homogeneous as a whole. In this case, it is preferable that the plurality of divided areas is divided according to the distance from the center of the bundle fiber.

Still further, in the probe according to the present invention, it is preferable that the light guide section includes at least one light guide plate having a connection surface to which at least some of the exit ends of the plurality of optical fibers are connected and an exit surface from which the measuring light entered from the connection surface exits. In this case, it is preferable that the light guide plate is provided in plurality and disposed across the acoustic wave transducer.

Further, in the probe according to the present invention, it is preferable that the homogenizer is a light shaping diffuser in which small lenses are disposed randomly on one side of a substrate.

Still further, it is preferable that the probe according to the present invention includes a holding section that integrally holds the light condensing member and the bundle fiber. In this case, it is preferable that the holding section integrally holds the homogenizer as well.

Further, it is preferable that the probe according to the present invention includes a holding section that holds the entrance end so as to cover the entrance face of the bundle fiber and has a window section at a portion where the measuring light enters. In this case, the window section may be formed of an ND filter.

Still further, in the case where the holding section is provided, it is preferable that the probe according to the present invention includes an aperture member having an aperture that allows the measuring light, which is to enter the bundle fiber, to pass through and an aperture member which is provided at the entrance end of the bundle fiber and gradually reduces the diameter of the aperture toward the entrance end to a size corresponding to the diameter of the bundle fiber. Alternatively, it is preferable that the holding section includes therein a light guide member formed of a cap member and a ring shaped chip made of a material resistant to optical energy and fitted around the cap member or a light guide member having an aperture stop and a relay lens system. Still further, it is preferable that the holding section includes a connector structure removably attachable to amounting section of an equipment housing which includes a light source.

A photoacoustic measurement apparatus of the present invention includes:

the probe described above; and a signal processing means that processes a photoacoustic signal of the photoacoustic wave detected by the acoustic wave transducer.

It is preferable that the photoacoustic measurement apparatus according to the present invention includes a light source that outputs the measuring light, an equipment housing having amounting section optically connected to the light source and holding the homogenizer, and a holding section that integrally holds the light condensing member and the bundle fiber, in which the mounting section and the holding section have connector structures removably attachable to each other. Alternatively, it is preferable that the photoacoustic measurement apparatus according to the present invention includes a light source that outputs the measuring light, an equipment housing having amounting section optically connected to the light source and holding the homogenizer and the light condensing member, and a holding section that holds the entrance end so as to cover the entrance face of the bundle fiber and has a window section at a portion where the measuring light enters, in which the mounting section and the holding section have connector structures removably attachable to each other.

Further, in the photoacoustic measurement apparatus according to the present invention, it is preferable that the signal processing means includes an acoustic image generation means that generates a photoacoustic image based on the photoacoustic signal. In this case, it is preferable that the acoustic wave transducer detects a reflected acoustic wave of a transmitted acoustic wave to the subject, and the acoustic image generation means generates a reflected acoustic wave image based on a signal of the reflected acoustic wave.

The acoustic wave detection probe and the photoacoustic measurement apparatus according to the present invention are characterized in that the light guide section includes a homogenizer that flat-tops an energy profile of the measuring light entered therein, a light condensing member that condenses the measuring light transmitted through the homogenizer, and a bundle fiber which includes a plurality of optical fibers and is disposed such that the measuring light transmitted through the light condensing member enters from an entrance end of the bundle fiber. This allows the flat-topped laser light to dividedly enter each optical fiber in the bundle fiber and damage to the end face of the bundle fiber due to local energy exceeding damage threshold energy to be prevented to a large extent. As a result of this, it is possible to transmit high energy light and eliminate imbalance in the amount of energy of light traveling through each of a plurality of optical fibers in photoacoustic measurements.

BEST MODE FOR CARRYING OUT THE INVENTION

Figure 1:
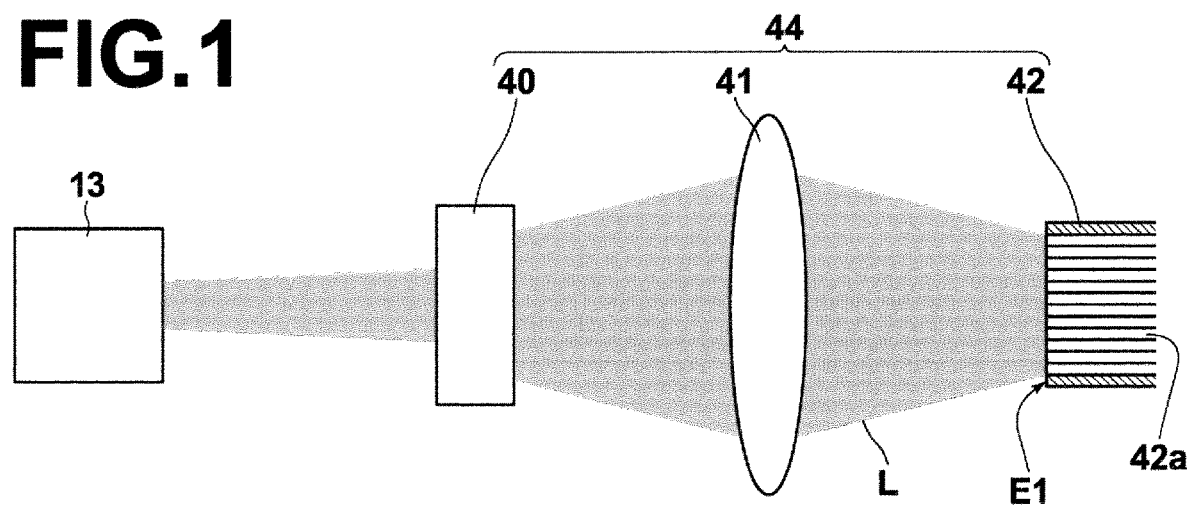
FIG. 1 is a schematic cross-sectional view, illustrating an example configuration of a light guide section of a probe of a first embodiment.

Hereinafter, embodiments of the present invention will be described with reference to the accompanying drawings, but it should be appreciated that the present invention is not limited to these embodiments. Note that each component in the drawings is not necessarily drawn to scale in order to facilitate visual recognition.

First Embodiment of Acoustic Wave Detection Probe

Figure 2:
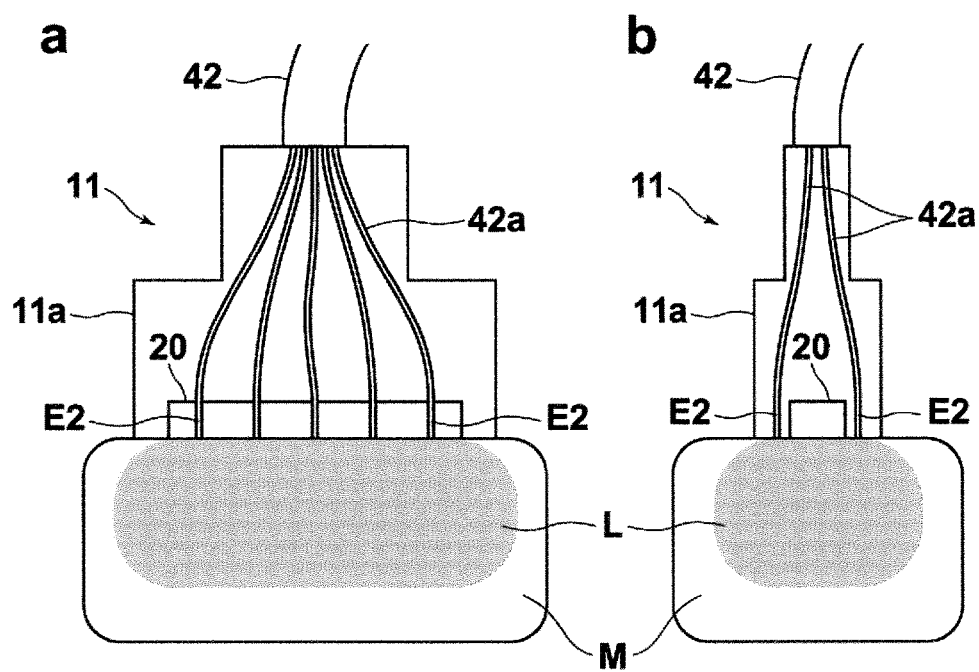
FIG. 2 is a schematic cross-section view, illustrating an arrangement of an acoustic wave transducer array and an optical fiber of the probe of the first embodiment.

A first embodiment of acoustic wave detection probe will be described first. FIG. 1 is a schematic cross-sectional view, illustrating an example configuration of a light guide section of the probe according to the present embodiment. FIG. 2 is a schematic cross-section view, illustrating an arrangement of an acoustic wave transducer array and an optical fiber of the probe of the present embodiment.

As illustrated in FIGS. 1 and 2, the probe 11 according to the present embodiment includes a light guide section 44 which is formed of a homogenizer 40, a light condensing member 41, and a fusion processed bundle fiber 42, an acoustic wave transducer array 20, and a housing 11a that holds an exit end E2 of the bundle fiber 42 and the acoustic wave transducer array 20. In the present embodiment, the probe 11 is used through optical connection to a laser unit 13 such that laser light L outputted from the laser unit 13 enters the homogenizer 40. The laser light L incident on the homogenizer 40 enters an entrance end E1 of the bundle fiber 42 via a light condensing member 41. Thereafter, the laser light L guided by the bundle fiber 42 exits from the exit end E2 of each optical fiber 42a in the bundle fiber 42 and is projected onto a subject M as measuring light. Note that the measuring light is not limited to laser light.

<Housing>

The housing 11a also functions as a holding member for the operator of the probe 11 to hold the probe 11. Although, the housing 11a has a hand-held shape in the present embodiment, the housing 11a of the present invention is not limited to this.

<Homogenizer>

In the present embodiment, the homogenizer 40 is an optical element that flat-tops the energy profile (energy distribution) of the laser light L entered from the upstream side of the optical system and diffuses the laser light L. The flat-topped laser light L is guided to the light condensing member 41, and enters the entrance end E1 with the flat-topped energy profile being maintained. To "flat-top" the energy profile is, in other words, to shape the laser light entered the homogenizer 40 so as to have a flat top energy profile near the center. The team "flat-top" as used herein refers to, when a concentric circle with a diameter of 80% of the beam diameter is taken in the energy profile of the laser light exiting from the homogenizer and the standard deviation is obtained with respect to the energy of each point within the concentric circle, the state in which the standard deviation is 25% or less of the average energy within the concentric circle. Generally, the homogenizer is formed such that the light is completely flat-topped (i.e., the standard deviation is nearly equal to 0) at infinity. In the present invention, the energy profile of the measuring light when entering the entrance end of the bundle fiber, however, is not necessarily in the state of completely flat-topped, and an energy profile which is in a flat-topped state to the extent of the range described above is sufficient. The flat-topped energy profile of the laser light L may prevent the light intensity from being locally intensified and damage in the bundle fiber 42 is also inhibited. Further, the imbalance between the energy of light enters each optical fiber is inhibited.

Further, the homogenizer 40 of the present embodiment also functions to diffuse the laser light L outputted from the laser unit 13 to increase the beam diameter of the laser light L, that is, to spread the distribution of propagation angles of light beams included in the laser light L. This causes the emission surface of the homogenizer 40 to serve as the secondary light source of the laser light L so that, when the laser light is condensed by the light condensing member 41, the laser light L is prevented from being focused too narrowly. The diffusion angle of the homogenizer 40 is preferably 0.2 to 5.0° and more preferably 0.4 to 3.0°. The reason for this is high transmission efficiency. The diffusion function of the homogenizer is not essential.

The distance between the homogenizer 40 and the light condensing member 41 is controlled appropriately such that the laser light L transmitted through the homogenizer 40 is efficiently coupled to the light condensing member 41. At this time, the homogenizer 40 is preferably disposed on the upstream side of the optical system with respect to the light condensing member 41 and within a range three times the focal length of the light condensing member 41 from the center thereof.

The homogenizer 40 may be formed of a single optical element or may be formed of a combination of a plurality of optical elements. In the case where the homogenizer 40 is fainted of a single optical element, for example, π Shaper available from AdlOptica may be used as the homogenizer 40. As for the homogenizer having a diffusion function, for example, a light shaping diffuser 53 having small concave lenses disposed randomly on one side 53s (FIG. 4) is preferably used. As for such light shaping diffusers, for example, Engineered Diffusers (Model Number: EDC-2.0-A, Diffusion Angle: 2.0°) available from RPC Photonics may be used. The use of such elements allows the energy profile and the shape of the laser light L to be changed almost arbitrarily. In this way, if the homogenizer 40 is formed of a single optical element, the light guide section 44 may be fainted of a simple structure.

Figure 3:
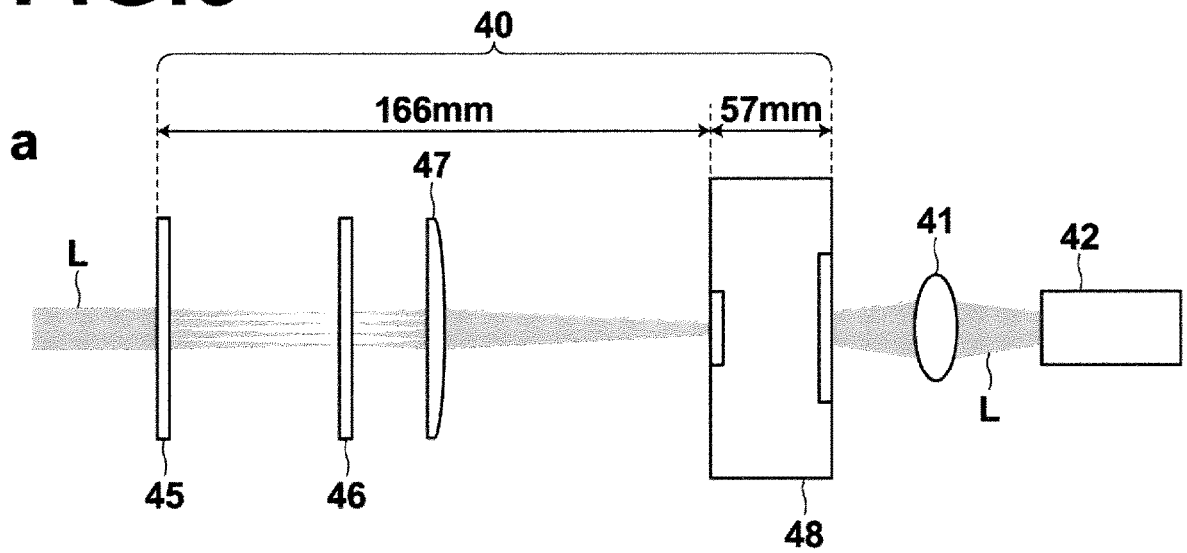
FIG. 3 shows schematic cross-sectional views, illustrating a plurality of example configurations of homogenizer.
Figure 3:
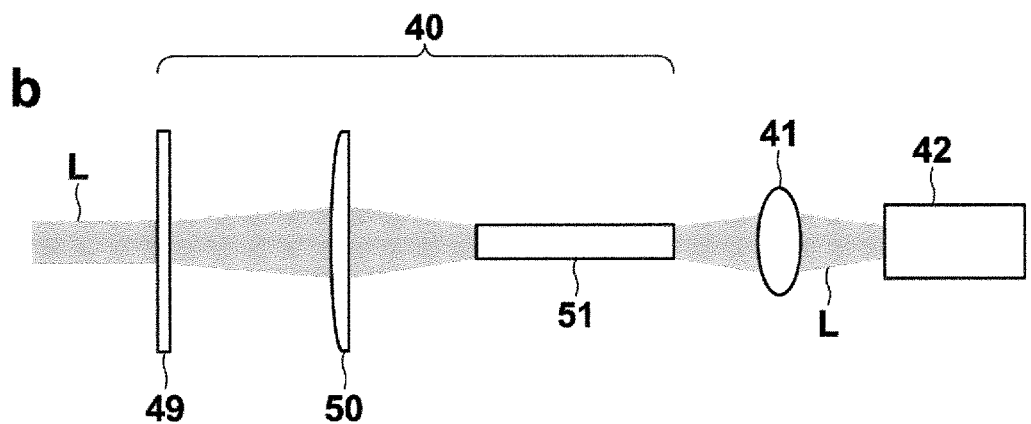
Figure 3:
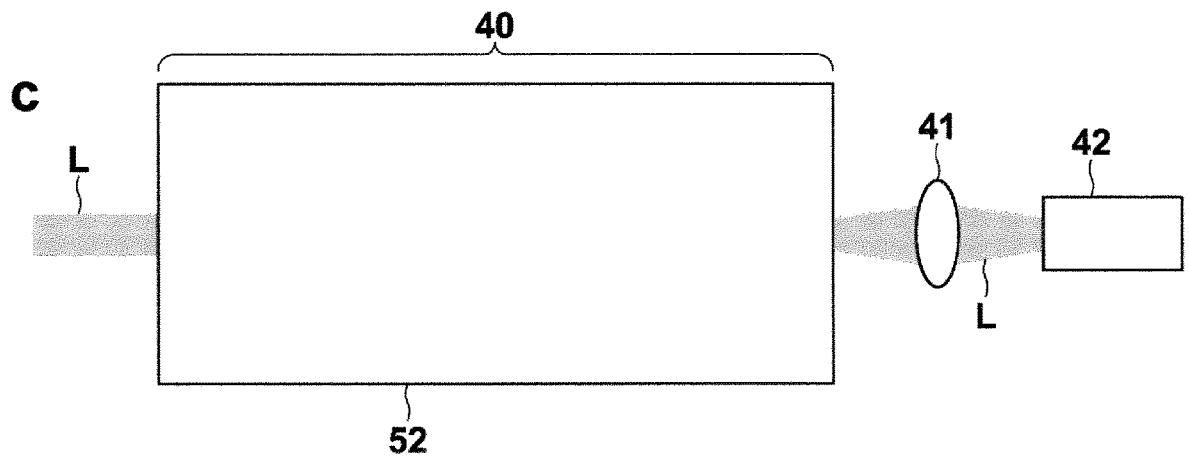

In the meantime, in the case where the homogenizer 40 is formed of a plurality of optical elements, for example, the following configuration may be cited. FIG. 3 shows schematic cross-sectional views, illustrating example configurations of the homogenizer 40. The homogenizer 40 may be fainted, for example, by arranging a microlens array A 45, a microlens array B 46, a planar-convex lens 47, and a variable beam expander 48 in the manner shown in a of FIG. 3. Further, the homogenizer 40 may also be formed by appropriately combining a holographic diffusion plate 49, a light focusing planar-convex lens 50, and a light pipe 51, as shown in b of FIG. 3. Still further, the homogenizer 40 may also be formed of a flat top laser beam shaper 52 which includes, for example, an aspherical lens for correcting beam energy profile, as shown in c of FIG. 3.

Figure 4:
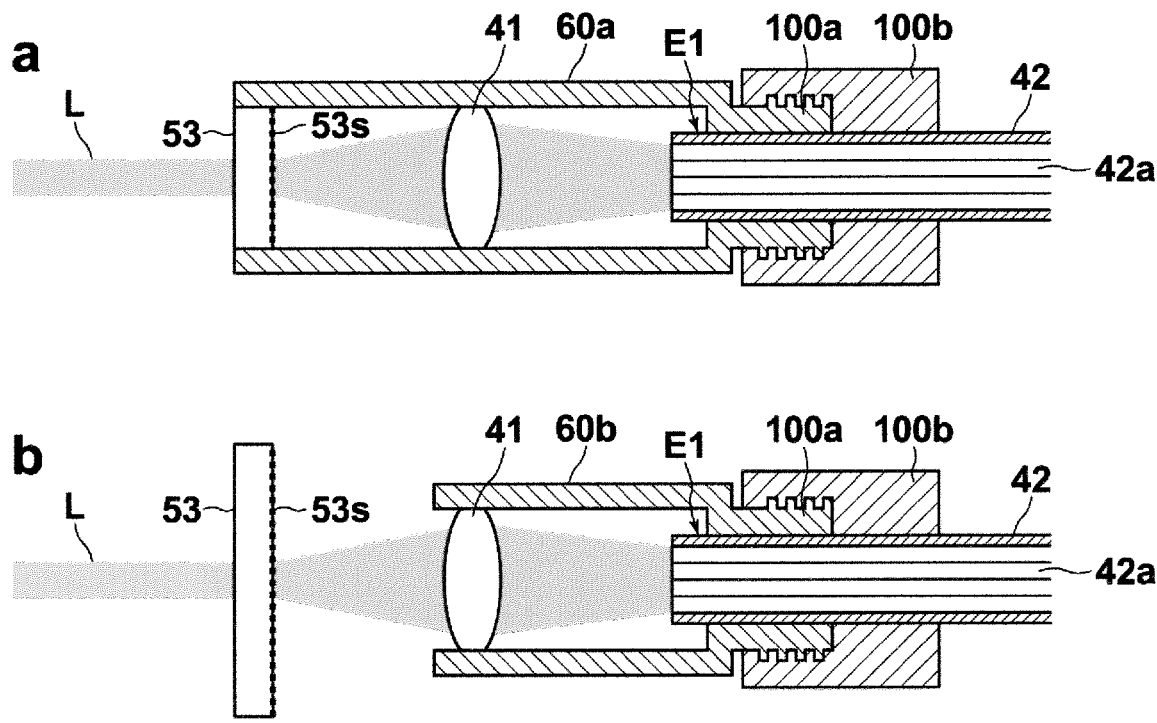
FIG. 4 shows schematic cross-sectional views, illustrating other example configurations of the light guide section of the probe.

The homogenizer 40 may be structured so as to be held integrally with the light condensing member 41 and the bundle fiber 42 by a holding section 60a, as shown in a of FIG. 4. This may eliminate the need to adjust the positional relationship between the homogenizer 40 and the light condensing member 41, whereby the optical system may be downsized.

<Light Condensing Member>

The light condensing member 41 guides the laser light L transmitted through the homogenizer 40 to the entrance end of the bundle fiber 42, and may be fainted of a condenser lens, a mirror, or a combination thereof. For example, in the present embodiment, the light condensing member 41 is a light condensing system formed of a single condenser lens. The focal length of the light condensing member 41 (distance between the principal point and the focal point on the side of the bundle fiber 42) is preferably 10 to 100 nm and more preferably 15 to 50 nm. The reason for this is that it allows downsizing of the optical system and conforms to numerical apertures NA (0.22 at maximum) of common optical fibers in which the core is formed of silica and the cladding is formed of fluorine-doped silica. Further, the light condensing member 41 may be a coupled lens system. If the light condensing member 41 is a coupled system lens, the focal length of the light condensing lens 41 refers to the combined focal length of the coupled system lens. The light condensing member 41 may be formed so as to be held integrally with the homogenizer 40 and the bundle fiber 42 by the holding section 60a, as shown in a of FIG. 4 or held integrally with only the bundle fiber 42 by the holding section 60a, as shown in b of FIG. 4.

<Bundle Fiber>

Figure 5:
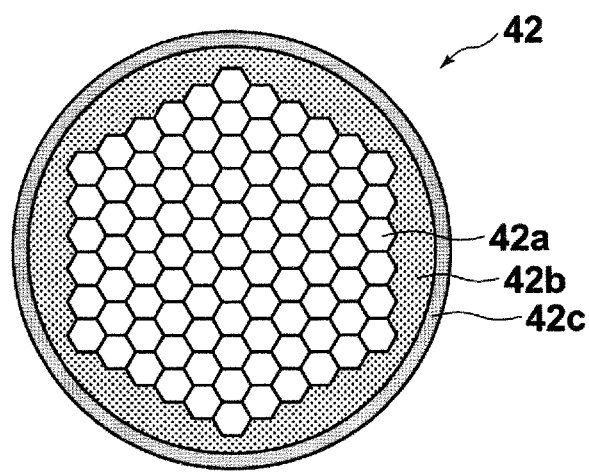
FIG. 5 is a schematic view, illustrating an end face arrangement of the entrance end of a fusion processed bundle fiber.

The bundle fiber 42 guides the laser light L condensed by the light condensing member 41 (i.e., transmitted through the light condensing member 41) near the acoustic wave transducer array 20. Note that the other light guide member may be provided between the light condensing member 41 and the bundle fiber 42. The bundle fiber 42 includes a plurality of optical fibers 42a, each having a core and a cladding, a covering member 42c, such as a ferrule, a sheath, and the like, and a filling member 42b filling between the outer circumferences of the plurality of optical fibers 42a and the covering member 42c, as illustrated, for example, in FIG. 5. The core diameter of each optical fiber 42a in the bundle fiber 42 is preferably 20 to 300 µm and more preferably 50 to 200 µm. There is not any specific restriction on the optical fiber 42a in the bundle fiber 42 but the optical fiber 42a is preferably a silica fiber.

Further, in the present embodiment, fusion processing is performed on at least the entrance end of the bundle fiber 42. The fusion processing is a bundling technology in which, when packing bear optical fibers into a bundle, the processing is performed not with an adhesive but heat and pressure. In a fusion processed bundle fiber, the claddings are fused together and the optical fibers are bundled in a hexagonal honeycomb shape and an extra gap between optical fibers is eliminated in comparison with the bundling with an adhesive. Therefore, this may provide an advantageous effect that the area occupied by the cores per unit area is increased. Also it may provide an advantageous effect that a material susceptible to optical energy is hidden so that the durability against optical energy is improved. From the viewpoint of further improving the durability against optical energy of the bundle fiber 42, the filling member 42b is preferably formed of a material having high durability against optical energy. Such a material may be a glass material, such as silica and the like. Such a bundle fiber may be produced by inserting a plurality of optical fibers into, for example, a cylindrical member of silica or the like, performing fusion processing on the cylindrical member, as well as the optical fibers, and thereafter covering the circumference with a covering member.

For example, the bundle fiber 42 is positioned such that the entrance end E1 thereof is located at the focal point of the light condensing member 41. A configuration may be adopted in which a bundle fiber positioning section (not shown in the drawing) that moves the bundle fiber in the directions of the optical axis thereof may be provided in order to allow a fine adjustment of the position of the bundle fiber 42. This allows the positional adjustment to be made near the focal point within the range in which the flat top state is not impaired and also allows the beam diameter when entering the entrance end E1 to be finely adjusted.

Further, if the homogenizer 40, the light condensing member 41, and the bundle fiber 42 are held integrally by the holding section 60a, as shown in a of FIG. 4, or if the light condensing member 41 and the bundle fiber 42 are held integrally by the holding section 60a, as shown in b of FIG. 4, the bundle fiber 42 is preferably fixed to the holding section 60a or 60b by a structure that allows the bundle fiber 42 to be removed from or attached to the holding section 60a or 60b, such as a screw structure, so that the entrance end E1 of the bundle fiber 42 is fixed easily at the focal point of the light condensing member 41. In FIG. 4, complementary screw structures are provided in the jointing section 100a of the hold section 60a or 60b on the side of the light condensing lens 41 and the jointing section 100b on the side of the bundle fiber 42, whereby the bundle fiber 42 is removably fixed to the holding section 60a or 60b. If the bundle fiber is fixed to the holding section 60a or 60b by, for example, the screw structures in the manner described above, the bundle fiber positioning section is not required and the optical system may be downsized. Further, the bundle fiber 42 may be replaced easily by simply unscrewing from the holding section 60a or 60b, the position readjustment between the light condensing member 41 and the bundle fiber 42 is unnecessary when replacing a damaged bundle fiber and the maintenability is improved. In order to integrate the light condensing member 41 and the bundle fiber 42 via the screw sections with the positional relationship being fixed, for example, the aspherical lens fiber collimator package (Model Number: F280SMA-A or F280SMA-B, Focal Length: 18.4 mm) available from Thorlabs, Inc. or the like may be used. Further, as the aspherical lens fiber collimator package series of Thorlabs, Inc. provides the products having focal lengths ranging from about 4 mm to 18.4 mm, it is possible to make an appropriate selection according to the purpose.

In order to improve homogeneity of the energy profile of the light projected onto the subject, exit ends E2 of a plurality of optical fibers 42a are disposed substantially evenly around the acoustic wave transducer array 20 on the exit side of the bundle fiber 42 according to the present embodiment.

<Acoustic Wave Transducer Array>

The acoustic wave transducer array 20 includes a plurality of acoustic wave transducers (or acoustic wave detection elements) disposed one-dimensionally or two-dimensionally and converts an acoustic wave signal to an electrical signal. The acoustic wave transducer is a piezoelectric element made of, for example, piezoelectric ceramics, piezoelectric single crystal, or a polymer film, such as a polyvinylidene fluoride (PVDF) film or the like. The term "acoustic wave" as used herein refers to include ultrasonic wave and photoacoustic wave. The term "ultrasonic wave" as used herein refers to an elastic wave generated in the subject by the vibration of the acoustic wave transducer array and a reflection wave thereof, and the term "photoacoustic wave" as used herein refers to an elastic wave generated in the subject by the photoacoustic effect due to the projection of measuring light. The acoustic wave transducer array 20 preferably includes acoustic elements, such as an acoustic matching layer, an acoustic lens, a backing member, and the like, in order to detect accurate acoustic wave signals.

<Control of Beam Diameter>

In the case where the homogenizer 40 has the diffusion function, the light condensing member 41 condenses laser light L (measuring light) such that a minimum beam diameter D (i.e., beam diameter on the focal plane) of the laser light L defined by Formula 3 below satisfies Formula 4 below in relation to a diameter d of the bundle fiber 42, and the bundle fiber 42 is preferably disposed such that the laser light L enters the bundle fiber 42 with the beam diameter D being 0.8 d to 1.2 d.

$$D = 2.5 \cdot f \cdot \tan\left(\sqrt{\left(\frac{\phi}{2}\right)^2 + \left(\frac{\theta}{2}\right)^2}\right) \quad \text{Formula 3}$$

$$0.8d \leq D \leq 1.2d \quad \text{Formula 4}$$

The reason why the minimum beam diameter D is set to 0.8 d or more is to inhibit damage to the entrance end E1

(core damage mode) of the bundle fiber 42 caused by energy concentration due to the focused beam diameter, and more specifically it is as follows.

Figure 6:
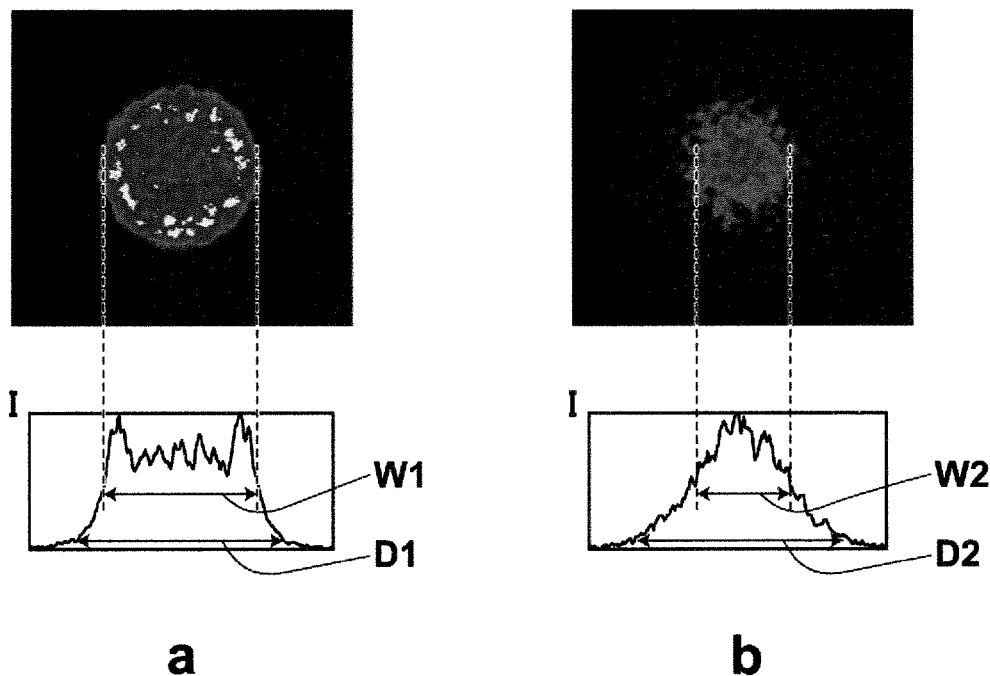
FIG. 6, a shows an energy profile of laser light flat-topped first by a homogenizer and then condensed by a lens, and b shows an energy profile of laser light only condensed by a lens without using a homogenizer.

An energy profile of the laser light L at the focal plane which is flat-topped first by the homogenizer 40 and then condensed by a lens is shown in a of FIG. 6. An energy profile of laser light only condensed by a lens without using the homogenizer 40 is shown in b of FIG. 6. From FIG. 6 it is known that the ratio of the full width at half maximum W1 to the minimum beam diameter D1 of the laser light in a of FIG. 6 is large in comparison with the ratio of the full width at half maximum W2 to the minimum beam diameter D2 of the laser light in b of FIG. 6. Generally, as the spread angle φ of the laser light L when outputted from the laser unit is small (about 0.15° at most), the condensed laser light L is focused to a small size at the entrance end E1 of the bundle fiber 42. As a result, the energy of the laser light L is concentrated at the entrance end of the bundle fiber 42 and damage occurs in the entrance end E1 of the bundle fiber 42.

Figure 7:
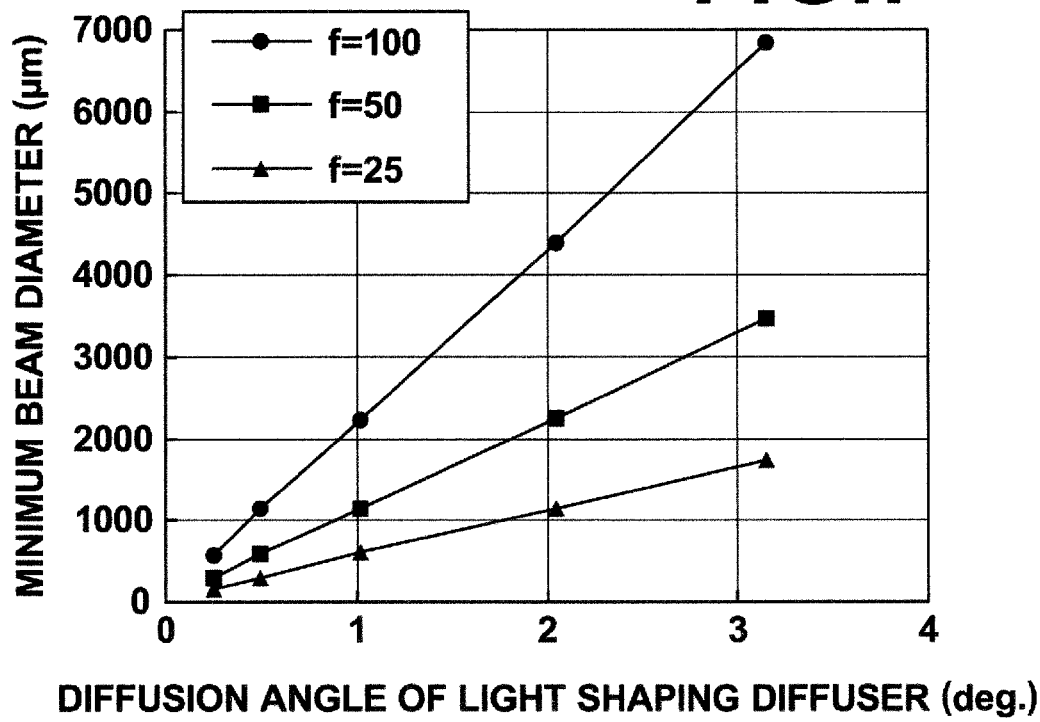
FIG. 7 is a graph illustrating a relationship between the optical property of a light shaping diffuser and light condensing member and the minimum beam diameter.

Consequently, in the present embodiment, the beam diameter of the laser light L at the focal position is controlled by diffusing the laser light L once by the homogenizer 40. FIG. 7 is a graph illustrating the relationship between the optical property of light shaping diffuser (Engineered Diffusers) and light condensing member and minimum beam diameter. The horizontal axis of the graph represents the diffusion angle (deg.) of the light shaping diffuser and the vertical axis represents the size of the minimum beam diameter (µm). The circular plots in the graph represent data when the focal length of the light condensing member is 100 mm, the square plots represent data when the focal length of the light condensing member is 50 mm, and the triangular plots represent data when the focal length of the light condensing member is 25 mm. It is known from FIG. 7 that the minimum beam diameter may be controlled by controlling the optical property of the homogenizer and the light condensing member.

Such beam diameter control method uses the principle that, when parallel light traveling in a direction that forms an angle α with the optical axis of a light condensing member is incident on the light condensing member having a focal length f, the position of the condensing point where the parallel light is condensed is displaced from the position of the focal point of the light condensing member and the distance between the condensing point and the focal point may be approximated by f·tan α.

If the angle famed by the traveling direction of a laser beam incident on a light condensing member and the optical axis of the light condensing member has a distribution, therefore, the laser beam is condensed at a position corresponding to each angle, so that the condensing range (including peripheral portion) of the entire laser light in which each condensing point is lapped is increased. For example, if a homogenizer having a diffusion function is disposed on the upstream side of a light condensing member, the angle distribution of the laser beam which was about φ/2 or less before entering the homogenizer is extended to within about $\sqrt{((\varphi/2)^2+(\theta/2)^2)}$ in terms of half angle, so that the entire condensing range of the entire laser light condensed thereafter by the light condensing member is further extended corresponding to this.

Further, considering that the $1/e^2$ diameter of the laser light is set to the beam diameter in the condensing range, it is presumed that the diameter of the condensing range $2f\cdot\tan(\sqrt{((\varphi/2)^2+(\theta/2)^2)})$ and the minimum beam diameter D has a certain correlation with each other.

Figure 8:
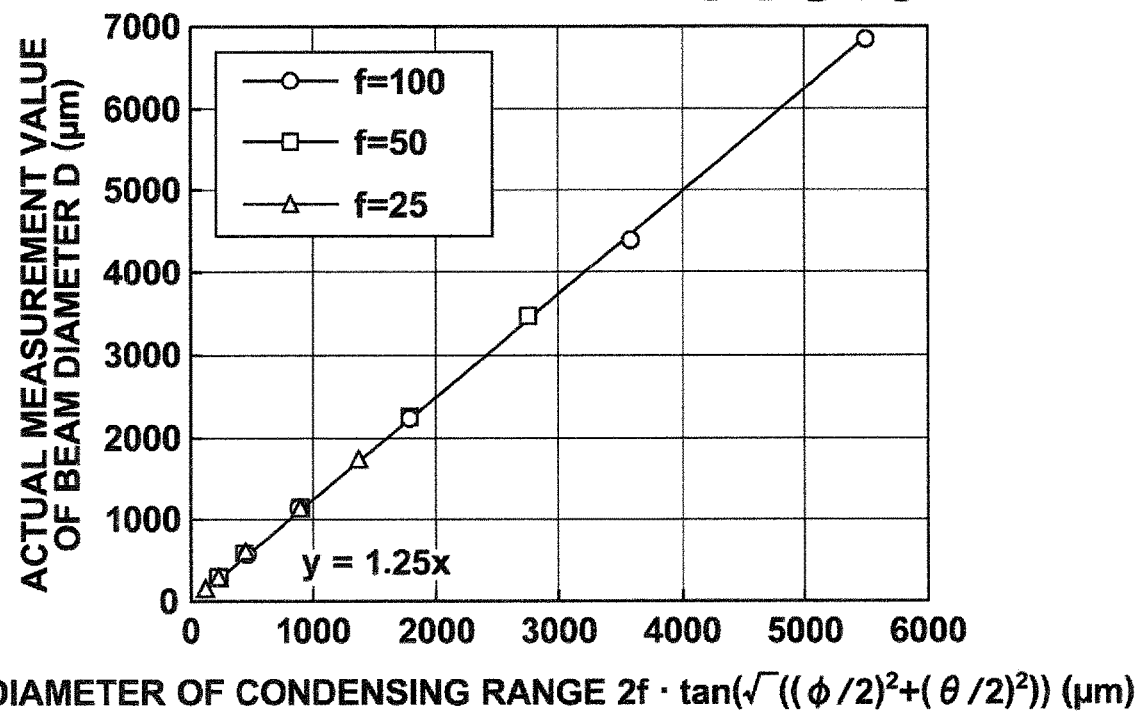
FIG. 8 is a graph illustrating, in the case where laser beam whose angle formed between the traveling direction thereof and the optical axis of a light condensing member has distribution is condensed by the light condensing member, a correlation between the diameter of condensing range and the minimum beam diameter.

FIG. 8 is a graph illustrating, in the case where laser beam whose angle formed between the traveling direction thereof and the optical axis of a light condensing member has distribution is condensed by the light condensing member, the correlation between the diameter of the condensing range $2f\cdot\tan(\sqrt{((\varphi/2)^2+(\theta/2)^2)})$ and the experimentally obtained actual minimum beam diameter D. More specifically, the graph shows results of experiment in which laser light having a wavelength of 532 nm and a pulse width of 3.5 ns with a beam diameter of 3.5 mm and a spread angle φ of 0.13° before being inputted to a homogenizer having a give diffusion angle θ, is inputted to the homogenizer, then the laser light is condensed by a light condensing lens having a given focal length f, and the condensing range is measured with a beam profiler (LaserCam-HR available from Coherent Inc.). The same beam profiler was used when the diffusion angle of the homogenizer was obtained. The five circular plots in the graph are the results of measurement with an optical system of a combination of a light condensing lens having a focal length f of 100 nm and a homogenizer, and diffusion angles θ of the homogenizer are 0.25, 0.50, 1.02, 2.05, and 3.15° from the left bottom plot. The five rectangular plots in the graph are the results of measurement with an optical system of a combination of a light condensing lens having a focal length f of 50 mm and a homogenizer, and diffusion angles θ of the homogenizer are 0.25, 0.50, 1.02, 2.05, and 3.15° from the left bottom plot. The five triangular plots in the graph are the results of measurement with an optical system of a combination of a light condensing lens having a focal length f of 25 nm and a homogenizer, and diffusion angles θ of the homogenizer are 0.25, 0.50, 1.02, 2.05, and 3.15° from the left bottom plot.

It is known from FIG. 8 that the minimum beam diameter D is in the relationship of linear function with the diameter of the condensing range. The slope of the linear function in the graph is about 1.25. Thus, the minimum beam diameter D is given by Formula 3 above.

That is, for a given laser light, it can be said that any minimum beam diameter D may be formed by appropriately setting the focal length f and the diffusion angle θ, not limited to the focal lengths and diffusion angles used in the experiment. Then, the wider the beam diameter, the more the energy density may be reduced.

In the present embodiment, it is possible to guide the high energy laser light L by the bundle fiber 42 without exceeding the damage threshold energy density of the entrance end of the bundle fiber 42 by controlling the minimum beam diameter D of the laser light L through the use of the relationship between the focal length of the light condensing member and the diffusion angle of the homogenizer.

In relation to the diameter d of the bundle fiber 42, the reason why the minimum beam diameter D is set to 1.2 d or less is to inhibit damage to a member surrounding the entrance end E1 of the bundle fiber 42 by absorbing the energy of the laser light L if the minimum beam diameter D is increased and to prevent emissions, such as dust, gas, and the like, from being released from the damaged region. Such emissions induce the destruction of the cores by adhering to the end face of the bundle fiber 42 and can be a cause of the problem that the energy transmission is hindered (ambient damage mode). That is, the reason why the minimum beam diameter D is set to 1.2 d or less is to inhibit the generation of the ambient damage mode described above. The member surrounding the bundle fiber refers to, for example, the filling material 42b made of resin, the covering member 42c, such as the metal ferrule covering the outer circumference of the filling member 42b, and the like.

The reason why the minimum beam diameter D exceeds d is that the portion in the range exceeding d is a peripheral portion (on the remote side from the optical axis) of the beam and has relatively weak light intensity, and therefore the ambient damage mode is unlikely to occur even the minimum beam diameter exceeds somewhat the diameter of the bundle fiber. The preferable range of the minimum beam diameter D is 0.8 d to 1.0 d. The reason why the bundle fiber 42 is disposed such that the laser light L enters the bundle fiber 42 with the beam diameter D being 0.8 d to 1.2 d is to efficiently input the laser light L condensed according to the diameter d of the bundle fiber 42 to the entrance end E1 of the bundle fiber 42.

As described above, in the acoustic wave detection probe according to the present embodiment, light (measuring light) is passed through the homogenizer once to flat-top the energy profile, and then the beam diameter of the laser light when entering the bundle fiber is controlled by the light condensing member. This allows the flat-topped laser light to dividedly enter each optical fiber in the bundle fiber and damage to the end face of the bundle fiber due to local energy exceeding the damage threshold energy density to be prevented to a large extent. The prevention of local damage leads to that more amount of energy may be injected as a whole from the viewpoint of energy transmission, and indicates that the energy is distributed appropriately to each optical fiber from the viewpoint of imbalance in the amount of optical energy. As a result of this, it is possible to transmit high energy light and eliminate imbalance in the amount of energy of light traveling through each of a plurality of optical fibers in photoacoustic measurements.

Second Embodiment of Acoustic Wave Detection Probe

Next, a second embodiment of the acoustic wave detection probe will be described. The probe of the present embodiment differs from the first embodiment in that the light guide section includes a beam expander optical system on the upstream side of the bundle fiber 42. Therefore, components identical to those of the first embodiment will not be elaborated upon further here unless otherwise specifically required.

Figure 9:
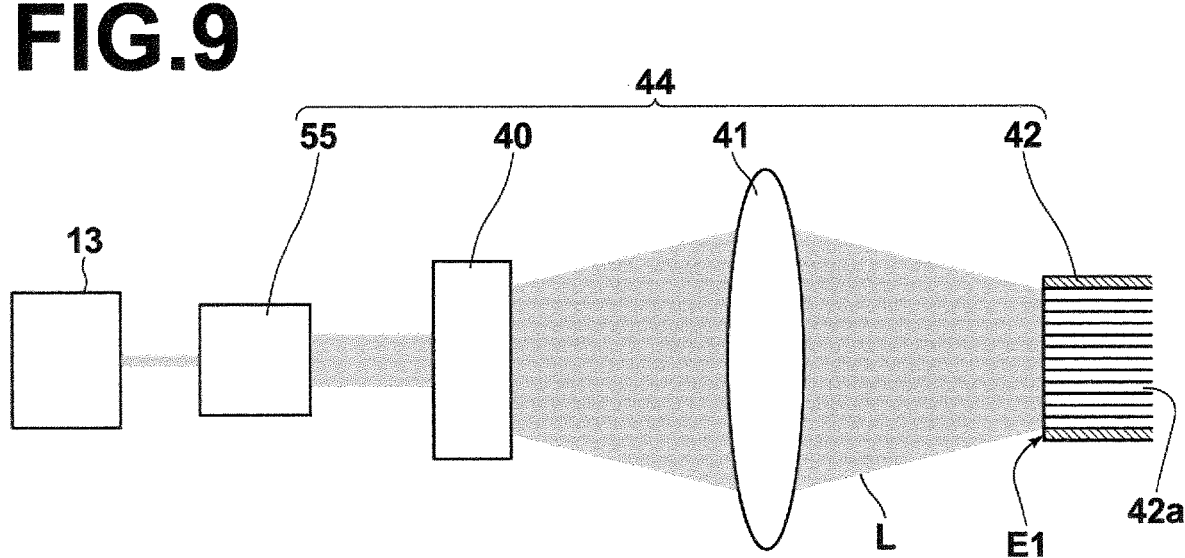
FIG. 9 is a schematic view of a light guide section which includes a beam expander, illustrating the configuration thereof.

FIG. 9 is a schematic view of the light guide section which include a beam expander, illustrating the configuration thereof.

The probe 11 according to the present embodiment includes a light guide section 44 which is formed of a beam expander 55, the homogenizer 40, the light condensing member 41, and the fusion processed bundle fiber 42, the acoustic wave transducer array, and the housing that holds the exit end of the bundle fiber 42 and the acoustic wave transducer array. In the present embodiment, the probe 11 is used through optical connection to the laser unit 13 such that laser light L outputted from the laser unit 13 enters the beam expander 55. The laser light L incident on the beam expander 55 enters the entrance end E1 of the bundle fiber 42 via the homogenizer 40 and the light condensing member 41. Thereafter, the laser light L guided by the bundle fiber 42 exits from the exit ends E2 of a plurality of optical fibers 42a in the bundle fiber 42 and is projected onto a subject M as measuring light.

The housing, homogenizer 40, the light condensing member 41, and the acoustic wave transducer array are identical to those of the first embodiment.

<Beam Expander Optical System>

The beam expander optical system 55 expands the measuring light to a beam diameter that conforms to the angular apertures of a plurality of optical fibers 42a in the bundle fiber 42 and further to an optimum beam diameter with respect to the angular apertures, as illustrated, for example, in FIG. 9. The term "beam diameter that conforms to the angular apertures of optical fibers" refers to a beam diameter in which, when light is condensed at the entrance end of the bundle fiber via the homogenizer and the light condensing member, the convergence angle of the light becomes close the angular apertures of the optical fibers. The term "optimum beam diameter with respect to the angular apertures of the optical fibers" refers to a beam diameter in which the convergence angle of the light becomes substantially equal to the angular apertures of the optical fibers at that time. The beam expander optical system 55 is disposed on the upstream side of the light condensing member 41 (i.e., on the light source side). The expansion factor of the beam expander optical system 55 is adjusted to the angular apertures of the plurality of optical fibers 42a so that the laser light L may be inputted to the entrance end E1 of the bundle fiber 42 with a wider spread angle within the range that does not exceed the numerical apertures of the optical fibers 42a. For example, the numerical aperture of a silica fiber having a general core/cladding structure is 0.20 to 0.22 and the angular aperture is 11.4 to 12.7°. By setting in this way, the spread angles of the light after exiting from an optical fibers 42a may be increased as wide as possible and the illumination may be homogenized at a shorter distance from the exit end faces of the optical fibers 42a. The beam expander optical system 55 may be disposed between the homogenizer 40 and the light condensing member 41, but the beam expander optical system 55 is preferably disposed at a position immediately upstream of the homogenizer 40 (immediately before the homogenizer 40), as shown in FIG. 9, from the viewpoint of control.

The beam expander optical system 55 described above may be produced by combining concave lenses and convex lenses, and the like, according to the numerical apertures of the optical fibers 42a.

As described above, also in the acoustic wave detection probe according to the present embodiment, light (measuring light) is passed through the homogenizer once to flat-top the energy profile, and then the beam diameter of the laser light when entering the bundle fiber is controlled by the light condensing member. This may provide identical effects to those of the first embodiment.

In addition, the measuring light is expanded to an optimum beam diameter with respect to the angular apertures of a plurality of optical fibers 42a in the bundle fiber 42 using the beam expander optical system 55 in the present embodiment, so that the homogeneity of illumination may further be improved.

Third Embodiment of Acoustic Wave Detection Probe

Next, a third embodiment of the acoustic wave detection probe will be described. The probe of the present embodiment differs from the first embodiment in that it projects light guided by the bundle fiber 42 via a light guide plate. Therefore, components identical to those of the first embodiment will not be elaborated upon further here unless otherwise specifically required.

Figure 10:
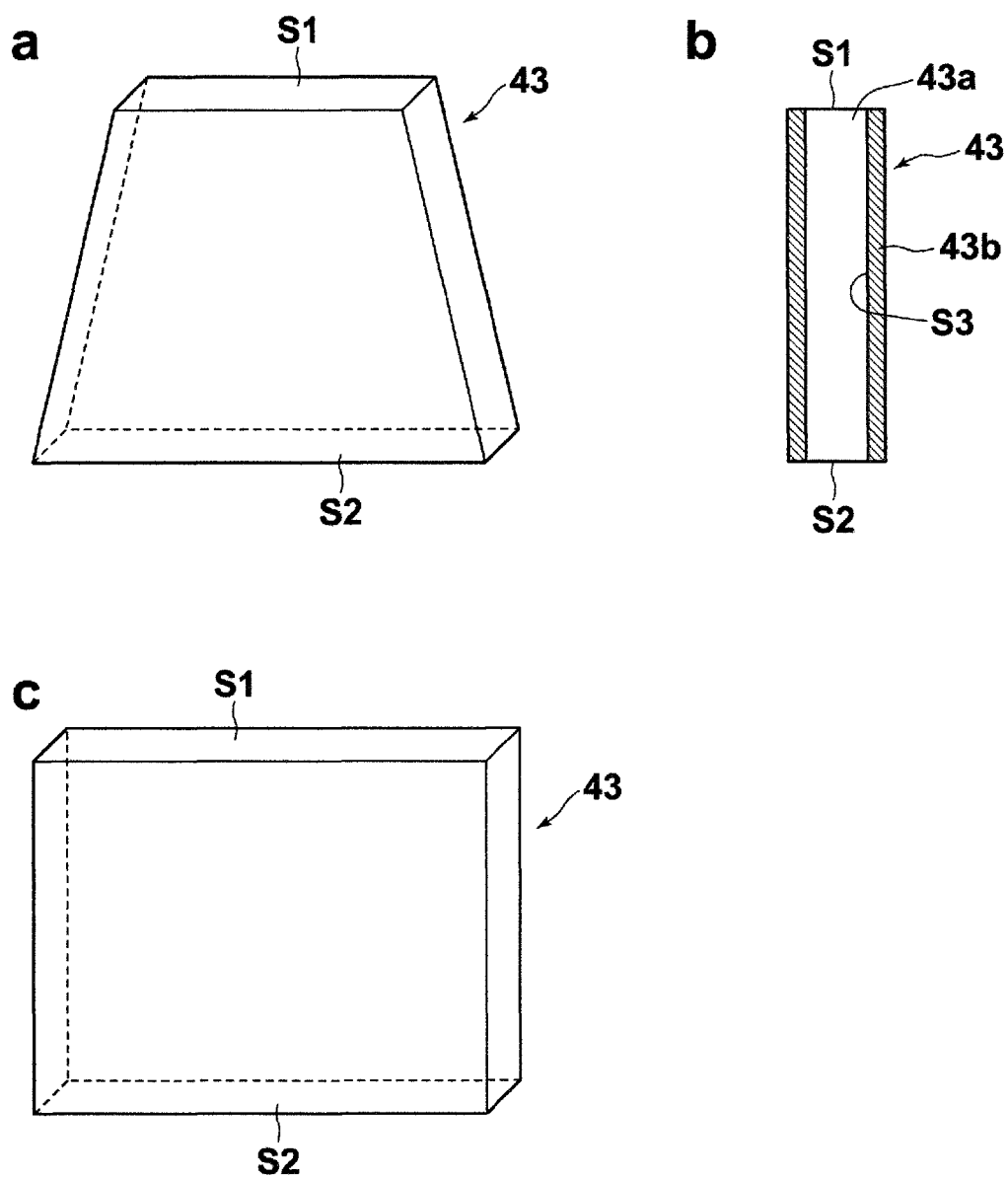
FIG. 10 is a schematic view illustrating light guide plate configuration examples.
Figure 11:
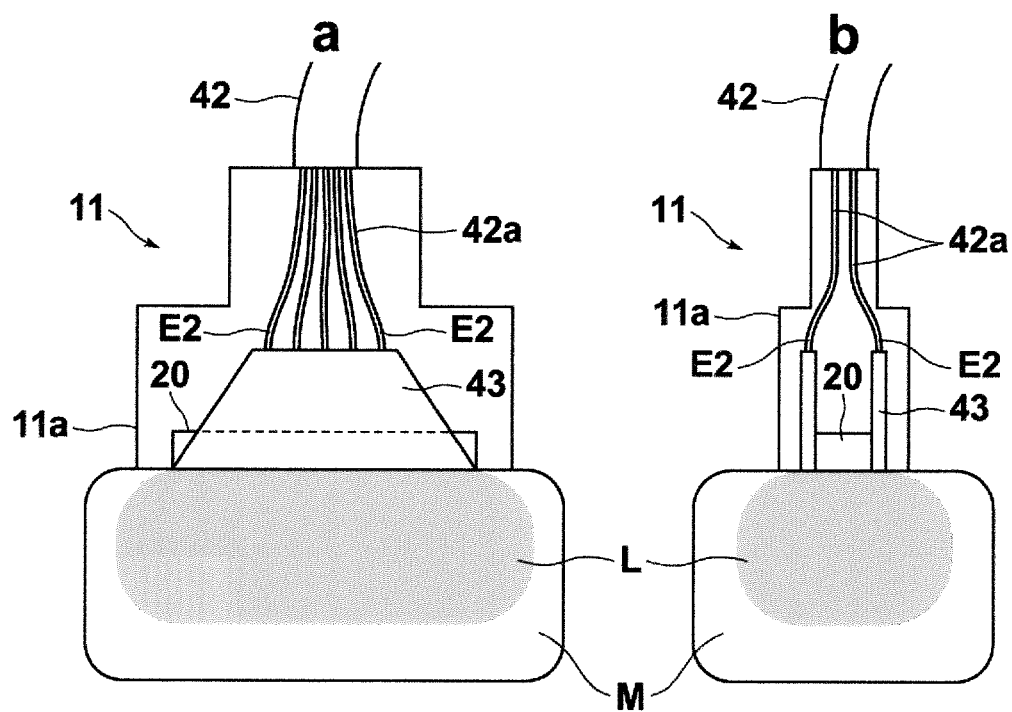
FIG. 11 is a schematic cross-section view illustrating an arrangement of an acoustic wave transducer and an optical fiber of the probe of the second embodiment.

FIG. 10 illustrates light guide plate configuration examples. FIG. 11 is a schematic view illustrating the arrangement of the acoustic wave transducer, the optical fibers, and the light guide plate in the probe of the present embodiment, in which a is a cross-sectional view viewed from the front and b is a cross-sectional view viewed from the side.

The probe 11 according to the present embodiment includes a light guide section which is formed of the homogenizer, the light condensing member, the fusion processed bundle fiber 42, and a light guide plate 43, the acoustic wave transducer array 20, and the housing 11a that holds the exit end E2 of the bundle fiber 42 and the acoustic wave transducer array 20. In the present embodiment, the probe 11 is used through optical connection to the laser unit such that laser light L outputted from the laser unit enters the homogenizer. The laser light L incident on the homogenizer enters the entrance end of the bundle fiber 42 via the light condensing member. Thereafter, the laser light L guided by the bundle fiber 42 is directly enters a connection surface S1 of the light guide plate from the exit ends E2 of a plurality of optical fibers 42a in the bundle fiber 42, then the laser light L guided by the light guide plate 43 exits from an exit surface S2 of the light guide plate and is projected onto a subject M as measuring light.

The housing, homogenizer, the light condensing member, and the acoustic wave transducer array 20 are identical to those of the first embodiment.

<Light Guide Plate>

The light guide plate 43 is, for example, an acrylic plate or a silica plate with a surface being specially processed to cause light entered from one end (connection surface S1) to be uniformly surface-emitted from the other end (exit surface S2). For example, the light guide plate 43 may be produced by forming thin resin films 43b having a low refractive index on a pair of opposite side surfaces of a silica plate 43a, as shown in FIG. 10. In this case, laser light entered from the connection surface S1 propagates while repeating reflections at the interface S3 between the silica plate 43a and the thin resin film 43b and exits from the exit surface S2. The exit ends E2 of the optical fibers 42a are disposed almost evenly on the connection surface S1 of the light guide plate 43 and optically connected thereto. As illustrated in a of FIG. 10, if the light guide plate 43 has a tapered shape that extends toward the exit surface S2 from the connection surface S1 of the light guide plate, it is possible to uniformly project the laser light L more extensively. Note that the light guide plate 43 may have a cuboid shape as shown in c of FIG. 10. As illustrated in FIG. 11, two light guide plates 43 are disposed so as to face to each other across the acoustic wave transducer array 20, and optical fibers 42a are connected to the connection surface S1 of each light guide plate 43 in the present embodiment. The light guide plate 43 may have, at a tip portion thereof, a mechanism that diffuses light (resin containing scattering particles or the like) or a mechanism that directs the traveling direction of light to the acoustic wave transducer array 20 (notch for refracting light or the like), so that the laser light L can be projected onto a wider range of the subject M.

As described above, also in the acoustic wave detection probe according to the present embodiment, light (measuring light) is passed through the homogenizer once to flat-top the energy profile, and then the beam diameter of the laser light when entering the bundle fiber is controlled by the light condensing member. This may provide identical effects to those of the first embodiment.

In addition, the measuring light is projected via the light guide plate in the present embodiment, so that the homogeneity of the energy profile of light projected on to the subject may further be improved.

<Design Changes of Probe>

In the present invention, the measuring light is passed through the homogenizer once to flat-top the energy profile. But, there may be a case in which it is difficult to make the energy profile completely flat-topped even in the case where the homogenizer is used. Consequently, it is preferable to consider the positions of optical fibers in the bundle fiber when disposing the exit ends of the optical fibers in the present invention.

Figure 12:
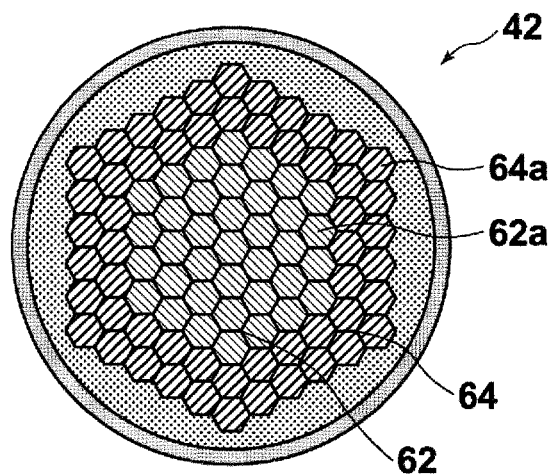
FIG. 12 illustrates a setting method of divided area divided in an end face arrangement of the entrance end of an optical fiber.
Figure 13:
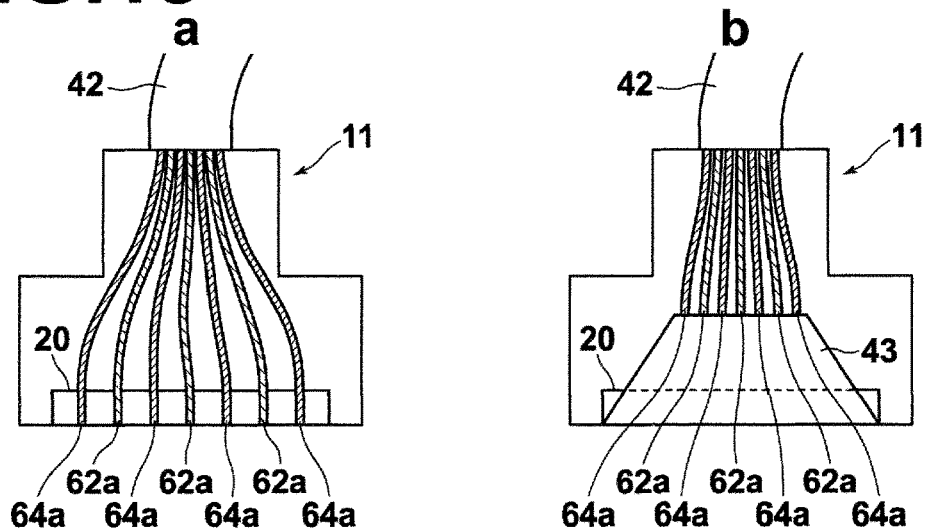
FIG. 13, a is a schematic view illustrating a design change in the arrangement of optical fiber in the probe of the first embodiment, and b is a schematic view illustrating a design change in the arrangement of optical fiber in the probe of the second embodiment.

For example, the energy profile of laser light is generally a Gaussian distribution centered on the optical axis. In this case, there may be a case in which local intensity imbalance which is dependent on the distance from the optical axis occurs even in the case where the homogenizer is used. More specifically, for example, in the energy profile shown in a of FIG. 6, there is a region where the intensity is gradually decreased from the flat-topped region to the periphery. Consequently, for example, a plurality of optical fibers is divided into a divided area close to the center of the bundle fiber 42 (center side area 62) and a divided area close to the periphery (peripheral side area 64) in the end face arrangement of the entrance end as shown in FIG. 12. Then, optical fibers 62a belonging to the center side area 62 and optical fibers 64a belonging to the peripheral side area 64 are uniformly disposed according to the relative magnitude with respect to each divided area. The term "disposed" here refers to include that the exit ends of the optical fibers 62a and 64a are evenly disposed around the acoustic wave transducer array 20, as shown, for example, in a of FIG. 13 and that the exit ends of the optical fibers 62a and 64a are evenly disposed on the connection surface of the light guide plate 43, as shown for example in b of FIG. 13. The term "uniformly according to the relative magnitude with respect to each divided area" to which the exit ends belongs as used herein refers to that the ratio of the numbers of the optical fibers of each divided area is not necessarily 1 to 1, and that the exit ends of optical fibers belonging to each divided area are disposed in a mixed manner as a whole according to the ratio of the number of optical fibers belonging to each divided area. This arrangement allows the local intensity imbalance described above to be inhibited and the homogeneity of the energy profile of the measuring light actually projected onto the subject to be improved.

The area division method is not limited to the above describe method and, for example, the bundle fiber may be divided into three areas according to the distance of the center thereof or divided into six equal areas with respect to the angle around the center thereof.

Figure 14:
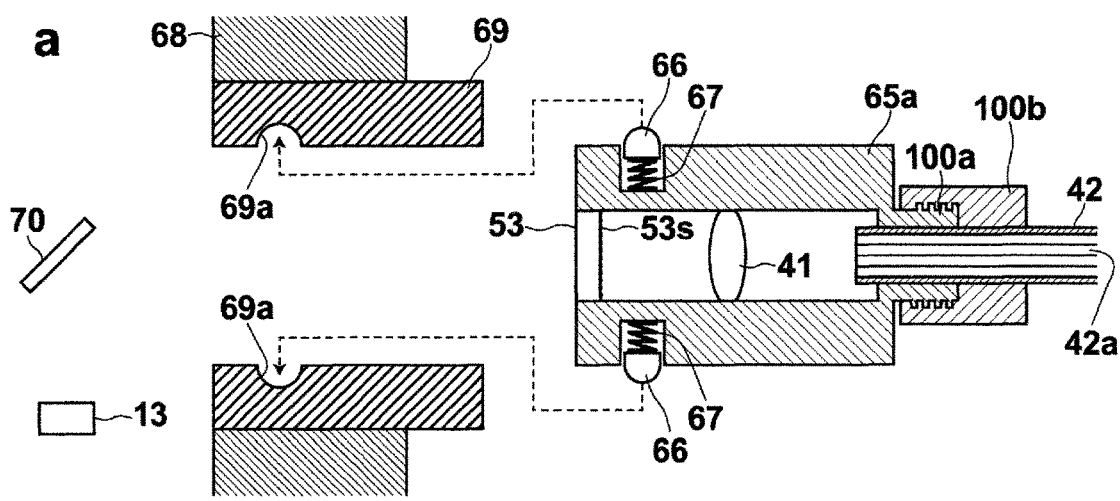
FIG. 14, a is a schematic view illustrating a configuration of a mounting section of an equipment housing which includes a light source, and a holding section and b is a schematic view illustrating that the holding section is mounted in the mounting section shown in a of FIG. 14.
Figure 14:
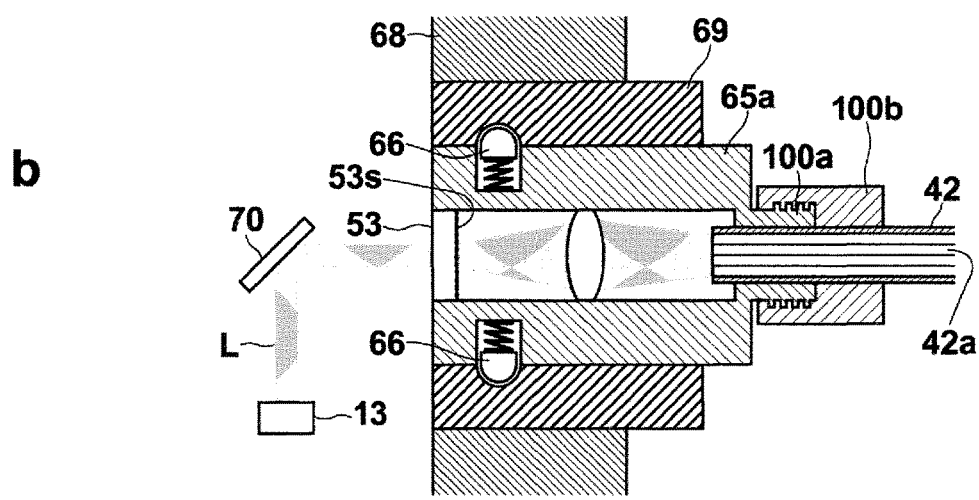

Further, in the case where the components of the light guide section are integrally held by the holding section, the holding section preferably has a connector structure removably attachable to amounting section of the equipment housing which includes a light source. For example, a of FIG. 14 is a schematic view illustrating the structure of a mounting section 69 of an equipment housing 68 which includes a laser unit 13 (light source) and a holding section 65a. The equipment housing 68 includes therein the laser unit 13, and the laser unit 13 and a light shaping diffuser 53 (homogenizer) are optically connected when the holding section 65a is mounted in the mounting section 69.

The connector structure of a holding section 65a is basically identical, for example, to that of the holding section 60a shown in a of FIG. 4 but differs in that it has a projection section 66 movable in up-down directions on the plane of the drawing by a resilient member 67, such as a spring or the like. The projection section 66 is pressed down into the slot of the holding section 65a when an external force is applied from above and returns back by the resilient power of the resilient member 67 when the external force is eliminated. Note that the surface of the protruding portion of the projection section 66 forms a curved surface so that the projection section 66 is also pressed down into the slot of the holding section 65a when an external force is applied from a horizontal direction on the plane of the drawing. In the meantime, the mounting section 69 is provided with an engaging section 69a which is, for example, a slot having a complementary shape with the projection section 66, as shown in a of FIG. 14. When insertion of the holding section 65a into the mounting section 69 is started, the projection section 66 is pressed down by the inner wall of the mounting section 69 and, thereafter, when the projection section 66 reaches the engaging section 69a, the projection section 66 returns back and engages with the engaging section 69a. Then, outputted laser light L is guided to the light shaping diffuser 53 by an optical system 70 and, thereafter, will propagate through the probe of the present invention.

Figure 15:
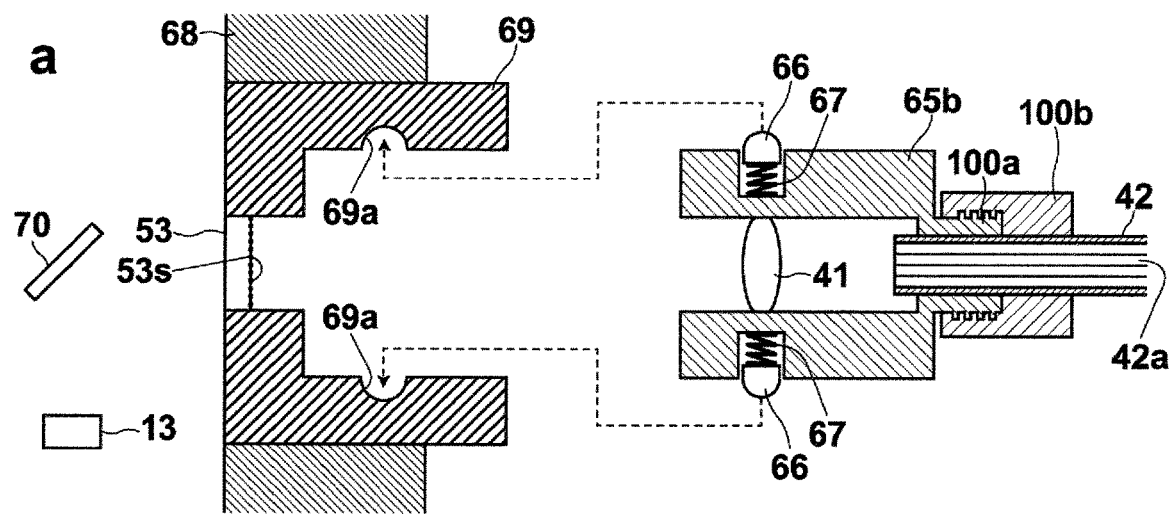
FIG. 15, a is a schematic view illustrating another configuration of a mounting section and a holding section of an equipment housing which includes a light source, and b is a schematic view illustrating that the holding section is mounted in the mounting section shown in a of FIG. 15.
Figure 15:
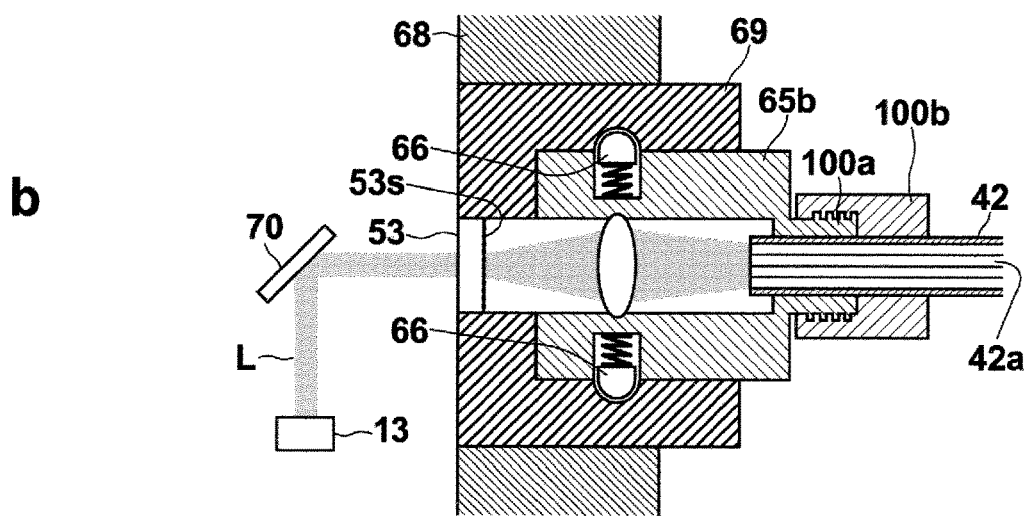

As an alternative example in which the holding section has a connector structure removably attachable to the mounting section, an embodiment shown in FIG. 15 may be cited.

The connector structure of a holding section 65b is basically identical, for example, to that of the holding section 60b shown in b of FIG. 4 but differs in that it has a projection section 66 movable in up-down directions on the plane of the drawing by a resilient member 67, such as a spring or the like. The projection section 66 is identical to the foregoing projection section. In the meantime, the mounting section 69 is provided with an engaging section 69a which is, for example, a slot having a complementary shape with the projection section 66 and a light shaping diffuser 53, as illustrated in a of FIG. 15. When insertion of the holding section 65b into the mounting section 69 is started, the projection section 66 is pressed down by the inner wall of the mounting section 69 and, thereafter, when the projection section 66 reaches the engaging section 69a, the projection section 66 returns back and engages with the engaging section 69a. At the same time, the positions of the light shaping diffuser 53 and the light condensing member 41 are fixed and can be optically connected. Then, outputted laser light L is guided to the light shaping diffuser 53 by an optical system 70 and, thereafter, will propagate through the probe of the present invention. This embodiment is preferable because only diffused measuring light is outputted from the equipment even when the probe is not connected.

Figure 16:
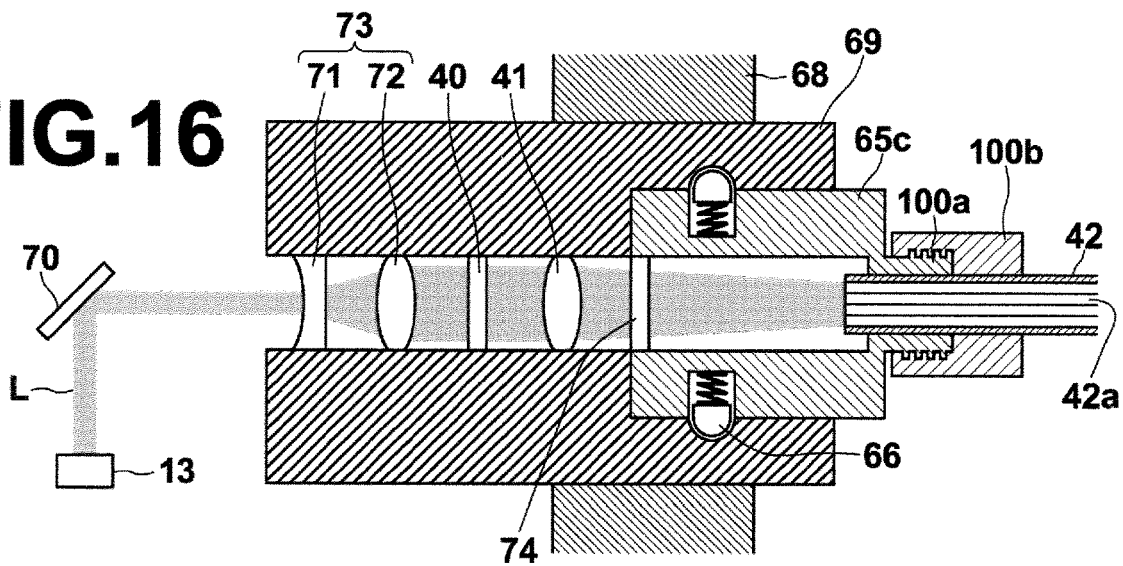
FIG. 16 is a schematic view illustrating another configuration of a mounting section and holding section of an equipment housing which includes a light source.

As still another example in which the holding section has a connector structure removably attachable to the mounting section, an embodiment shown in FIG. 16 may be cited.

For example, a holding section 65c holds the entrance end so as to cover the entrance face of the bundle fiber 42, and has a projection section 66 identical to the foregoing projection section and a window section 74 at a portion where the laser light L enters. The window section 74 is famed of an optically transparent material (e.g., silica) and provided on the optical path of the laser light L so as to block up a groove accommodating the entrance face of the bundle fiber 42. This causes, for example, the entrance face of the bundle fiber 42 to be placed in a space sealed by the holding section 65c. The surface of the window section 74 on the light source side preferably has an anti-reflection coat (ARcoat), such as $MgF_2$ film, $Ta_2O_5$ film, or $SiO_2$ multilayer film. In the meantime, the mounting section 69 is provided with, for example, a beam expander 73, a homogenizer 40, and a light condensing member 41, other than an engaging section 69a which is a slot having a complementary shape with the projection section 66, as shown in FIG. 16. The beam expander 73 is formed of, for example, a planar-concave lens 71 and a convex lens 72. The mounting procedure of the holding section 65c in the mounting section 69 is identical to that described above. When the holding section 65c is mounted in the mounting section 69, laser light L passed through the beam expander 73, homogenizer 40, and light condensing member 41 enters the entrance face of the bundle fiber 42 by transmitting through the window section 74. As adherence of dust and the like occurs on the light source side surface of the window section 74 having a low energy density in comparison with the entrance face of the bundle fiber 42, this embodiment has an advantageous effect that end face damage is unlikely to occur. Also in FIG. 14 or 15, identical effect may be obtained if a window section is provided. As the light condensing member 41 is installed on the light source system side, the embodiment also proves an advantageous effect that, when the holding section 65c is attached to the mounting section 65, the angular accuracy requirement for the holding section 65c is relaxed and only the positional accuracy needs to be primarily considered.

Further, an ND filter may be used as the window section 74 in FIG. 16. For example, the ND filter is a silica substrate coated with a multilayer oxide film. In such a case, the intensity of the laser light L may be reduced on the probe side and an adjustment mechanism for laser light intensity is unnecessary on the light source system side.

Figure 17:
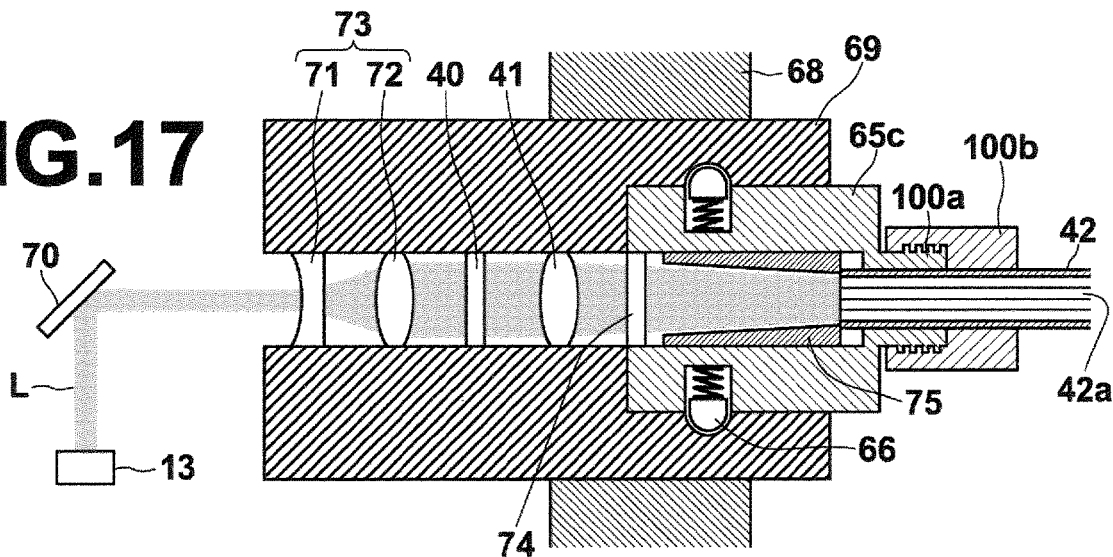
FIG. 17 is a schematic view illustrating a configuration in which an opening member is provided in the holding section.

As shown, for example, in FIG. 17, the holding section preferably has an aperture member having an aperture that allows the measuring light, which is to enter the bundle fiber, to pass through and a taper structure at the entrance end of the bundle fiber 42. The aperture diameter is formed so as to be gradually reduced toward the entrance end to a size corresponding to the diameter of the bundle fiber. For example, the aperture diameter of the aperture member 75 on the bundle fiber side corresponds to the diameter of the bundle fiber in FIG. 17. The taper angle of the taper structure is preferably larger than the convergence angle of light entering the bundle fiber 42 and smaller than the NA of the optical fiber. The inner surface of the aperture member 75 is formed to reflect, scatter, or absorb light. If the aperture inner surface reflects or scatters light, an angular light component outside the incident angle range within which the optical fibers can receive light becomes able to enter the optical fibers by way of the reflection or the scattering, so that the light transmission efficiency is further improved. In the meantime, if the aperture inner surface absorbs light the light of angular component outside the incident angle which can be received by the optical fibers is absorbed at a location away from the optical fibers and by a wide area, so the damage to the optical fibers is more inhibited than in the case where the absorption takes place adjacent to the optical fibers.

In order to cause the aperture inner surface to reflect light, for example, it is only necessary to perform smoothing processing, such as mirror finish and the like, or to form a high reflective film, such as a gold thin film or the like, on the aperture inner surface. Further, in order to cause the aperture inner surface to scatter light, it is only necessary to form the aperture member with, for example, a pressurized powder body or a sintered body of ceramics, such as $Al_2O_3$, $TiO_2$, $ZrO_2$, or the like, or with Teflon® or unpolished glass. In order to cause the aperture inner surface to absorb light, it is only necessary to form the aperture member with, for example, a metal such as aluminum, brass, copper, or the like.

Figure 18A:
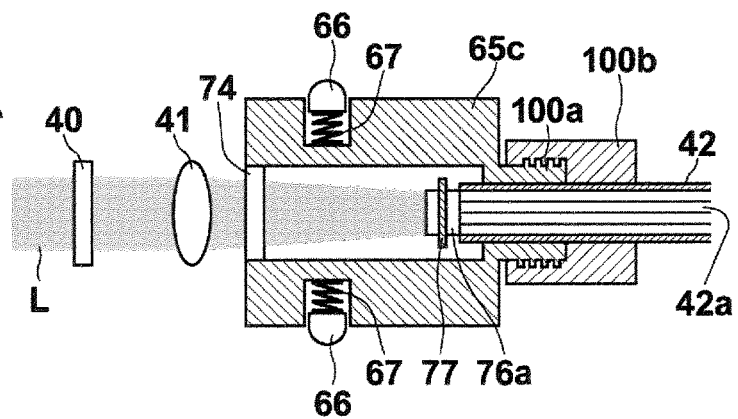
FIG. 18A is a schematic view illustrating a configuration in which a cap member (silica rod) is provided at the entrance end of the bundle fiber.
Figure 18B:
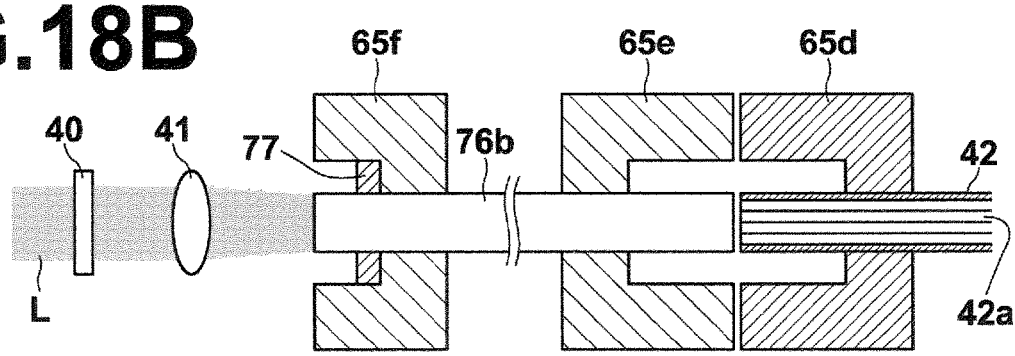
FIG. 18B is a schematic view illustrating a configuration in which a cap member (air gap optical fiber) is provided at the entrance end of the bundle fiber.
Figure 19:
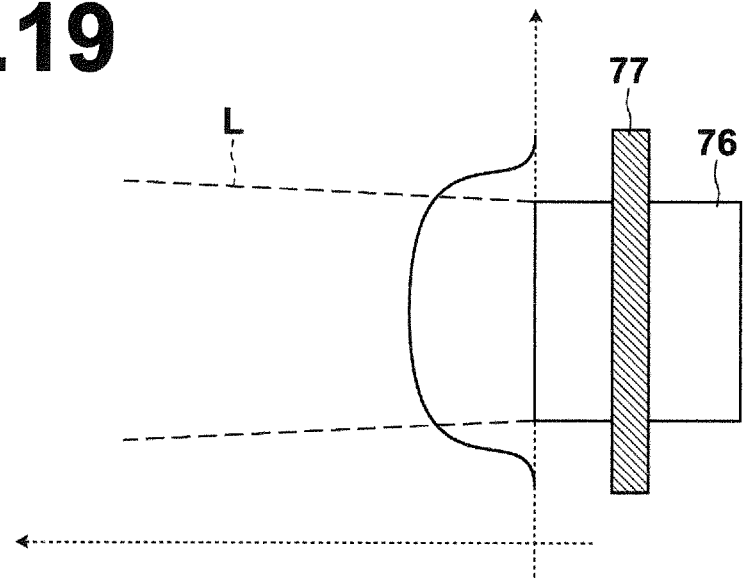
FIG. 19 is a schematic view illustrating the relationship between the energy profile of input beam and the cap member.
Figure 20:
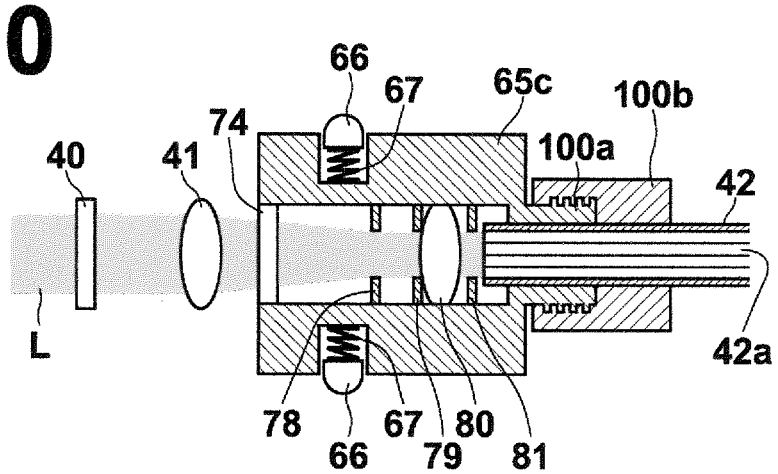
FIG. 20 is a schematic view illustrating a configuration in which a relay lens system is provided at the entrance end of the bundle fiber.

In the case where the ambient damage mode is likely to occur due to the influence of the peripheral portion of the energy profile, it is preferably to provide a light guide member for preventing damage to surrounding members of the bundle fiber (ferrule and the like) as shown, for example, in FIG. 18A, 18B, or 20. For example, the light guide member shown in FIG. 18A or 18B is formed of a cap member and a ring shaped chip 77 made of a material resistant to optical energy (e.g., high light absorption sapphire in the wavelength range of measuring light used) and fitted around the cap member. As for the cap member, for example, a silica rod 76a (FIG. 18A) or an air gap optical fiber 76b (FIG. 18B) may be used. The chip 77 is fitted around the entrance end of the cap member. If the air gap optical fiber 76b is used, in particular, it is preferable that the chip 77 is embedded in the connector of the air gap optical fiber 76b. For example, the air gap optical fiber 76b shown in FIG. 18B is provided with an exit side connector 65e removably attachable to a connector 65d of the bundle fiber 42 and an entrance side connector 65f, and the chip 77 is embedded at least in the entrance side connector 65f. The use of such a light guide member allows the light in the peripheral portion to be blocked, for example, through absorption or reflection by the chip 77 (FIG. 19). Consequently, the light at the peripheral portion is prevented from reaching the surrounding members of the bundle fiber and the ambient damage mode is prevented from occurring.

In the meantime, the light guide member shown in, for example, FIG. 20 is formed of a first aperture stop 78 (for blocking peripheral portion), a second aperture stop 79 (for adjusting light intensity), a relay lens system 80, and a third aperture stop 81 (for blocking peripheral portion). For example, the first aperture stop 78 is disposed adjacent to the focal point of the light condensing member 41, the second aperture stop 79 is disposed adjacent to the relay lens system 80, and the third aperture stop 81 is disposed adjacent to the entrance end of the bundle fiber. The use of such a light guide member allows the beam diameter to be enlarged or reduced before and after the relay lens system 80, and if the diameter of the bundle fiber differs depending on the probe used, the beam diameter may be adjusted to a desired size by adjusting the relay lens system 80. The peripheral portion of light is blocked by the first aperture stop 78 and the third aperture stop 81, while the second aperture stop 79 is used for light intensity adjustment.

Further, for example, the light guide member formed of the silica rod 76a and chip 77 (FIG. 18A), and the light guide member formed of the aperture stops 78, 79, 81 and the relay lens system 80 (FIG. 20) may also be provided in the holding member shown in FIG. 4, 14, or 15.

The provision of the connector structure in the holding section which is removably attachable to the mounting section as described above may improve convenience as a probe. Note that the connector structure is not limited to those described above and it is preferable that the holding section is compact.

First Embodiment of Photoacoustic Measurement Apparatus

Figure 21:
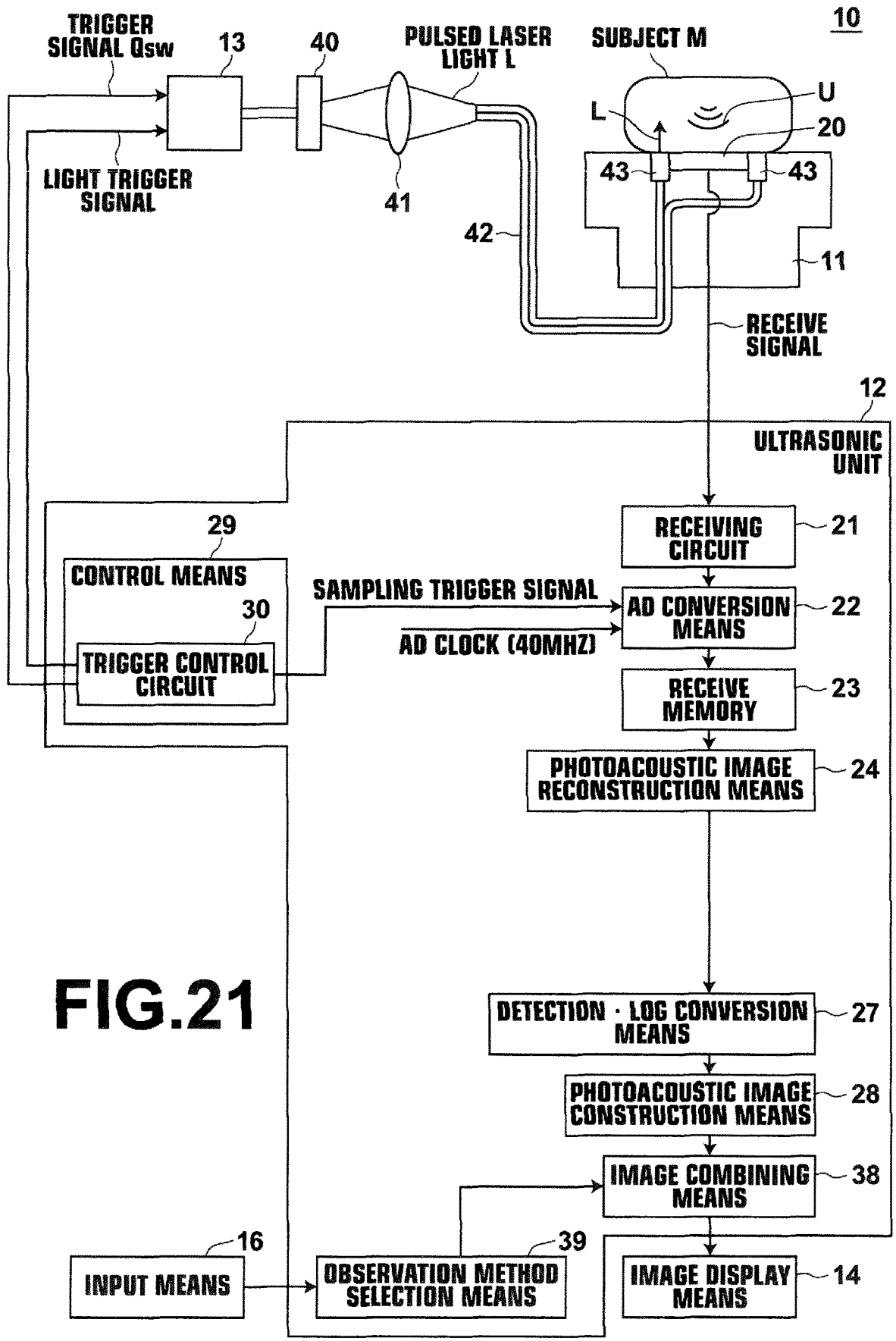
FIG. 21 is a schematic view illustrating a first embodiment of a photoacoustic image generation apparatus, as a photoacoustic measurement apparatus.

Next, a first embodiment of photoacoustic measurement apparatus will be described. In the present embodiment, a detailed description will be made of a case in which the photoacoustic measurement apparatus is a photoacoustic image generation apparatus that generates a photoacoustic image based on photoacoustic signals. FIG. 21 is a block diagram of the photoacoustic image generation apparatus 10 of the present embodiment, illustrating the configuration thereof.

The photoacoustic image generation apparatus 10 of the present embodiment includes a probe 11 according to the present invention, an ultrasonic unit 12, a laser unit 13, an image display means 14, and an input means 16.

<Laser Unit>

The laser unit 13 corresponds to the light source of the present invention and outputs, for example, laser light L as measuring light to be projected onto a subject M. The laser unit 13 is configured to output the laser light L, for example, by receiving a trigger signal from a control means 29. The laser light L outputted from the laser unit 13 is guided to the probe 11 using a light guide means, such as optical fiber, and projected onto the subject M from the probe 11. Preferably, the laser unit 13 outputs pulsed light with a pulse width of 1 to 100 nsec as the laser light.

Preferably, the pulse width tp (ns) of the laser light L satisfies Formula 5 below. Here, λ is the pulse energy (J) of the laser light used when entering the bundle fiber, λ is the wavelength (nm) of the laser light used, G is the damage threshold energy density (J/mm²) of the bundle fiber, λG and tG are respectively the wavelength and the pulse width of the laser light for which the damage threshold energy density is obtained, and d is the diameter of the bundle fiber. The reason for the above is that Formula 6 below is preferably satisfied in order to prevent the end face damage of the bundle fiber.

$$\left(\frac{4Ad^2}{\pi G}\frac{\lambda_G}{\lambda}\right)^2 t_G < t_P \qquad \text{Formula 5}$$

$$A < \pi\left(\frac{d}{2}\right)^2 G\left(\frac{\lambda}{\lambda_G}\right)\sqrt{\frac{t_P}{t_G}} \qquad \text{Formula 6}$$

For example, the laser unit 13 is a Q-switch (Qsw) alexandrite laser in the present embodiment. In this case, the pulse width of the laser light L is controlled, for example, by the Qsw. The wavelength of the laser light is determined appropriately based on the light absorption characteristics of the measurement target substance within the subject. If the measurement target is hemoglobin in a living body (i.e., if blood vessel is imaged) the wavelength, in general, is preferably belongs to near infrared wavelength range. The near infrared wavelength range refers to the wavelength range of about 700 to 800 nm. The laser light L may have a single wavelength or a plurality of wavelengths (e.g., 750 nm and 800 nm). If the laser light has a plurality of wavelengths, these wavelengths of light may be projected onto the subject M simultaneously or alternately by switching.

<Probe>

The probe 11 is a probe of the present invention that detects photoacoustic wave U generated in the subject M and it is the probe according to the third embodiment in the present embodiment.

<Ultrasonic Unit>

The ultrasonic unit 12 includes a receiving circuit 21, an AD conversion means 22, a receive memory 23, a photoacoustic image reconstruction means 24, a detection·log conversion means 27, a photoacoustic image construction means 28, the control means 29, an image combining means 38, and an observation method selection means 39. For example, the receiving circuit 21, AD conversion means 22, receive memory 23, photoacoustic image reconstruction means 24, detection·log conversion means 27, and photoacoustic image construction means 28 correspond, as a unit, to the acoustic image generation means of the present invention.

The control means 29 controls each section of the photoacoustic image generation apparatus 10 and includes a trigger control circuit 30 in the present embodiment. The trigger control circuit 30 sends a light trigger signal to the laser unit 13 when, for example, activating the photoacoustic image generation apparatus. This causes a flash lamp in the laser unit 13 to be turned on and excitation of the laser rod is started. The excitation state of the laser rod is maintained and the laser unit 13 becomes ready to output pulsed laser light.

Then, the control means 29 subsequently sends a Qsw trigger signal to the laser unit 13 from the trigger control circuit 30. That is, the control means 29 controls the output timing of the pulsed laser light from the laser unit 13 by the Qsw trigger signal. Further, the control means 29 sends a sampling trigger signal to the AD conversion means 22 simultaneously with the transmission of the Qsw trigger signal in the present embodiment. The sampling trigger signal serves as a timing signal to start sampling of the photoacoustic signal in the AD conversion means 22. In this way, the use of the sampling trigger signal allows the photoacoustic signal to be sampled in synchronization with the output of the pulsed laser light.

The receiving circuit 21 receives a photoacoustic signal detected by the probe 11. The photoacoustic signal received by the receiving circuit 21 is sent to the AD conversion means 22.

The AD conversion means 22 is a sampling means, and samples the photoacoustic signal received by the receiving circuit 21 and converts it to a digital signal. For example, the AD conversion means 22 includes a sampling control section and an AD converter. The receive signal received by the receiving circuit 21 is converted to a digitized sampled signal by the AD converter. The AD converter is controlled by the sampling control section and configured to perform sampling when a sampling trigger signal is received by the sampling control section. The AD conversion means 22 samples the receive signal at a predetermined sampling period based on, for example, an AD clock signal of predetermined frequency inputted from outside.

The receive memory 23 stores the photoacoustic signal sampled by the AD conversion means 22 (i.e., the sampled signal described above). Then, the receive memory 23 outputs the photoacoustic signal detected by the probe 11 to the photoacoustic image reconstruction means 24.

The photoacoustic image reconstruction means 24 reads the photoacoustic signal from the receive memory 23 and generates data of each line of a photoacoustic image based on the photoacoustic signal detected by the acoustic wave transducer array 20 of the probe 11. The photoacoustic image reconstruction means 24 generates data of one line by adding up, for example, data from 64 acoustic wave transducers of the probe 11 at delay times corresponding to the positions of the acoustic wave transducers (delay-and-sum method). The photoacoustic image reconstruction means 24 may perform the reconstruction by the CBP (Circular Back Projection) method in place of the delay-and-sum method. Otherwise, the photoacoustic image reconstruction means 24 may perform the reconstruction by the Hough transform method or the Fourier transform method.

The detection·log conversion means 27 obtains an envelope of the data of each line and performs log conversion on the obtained envelope.

The photoacoustic image construction means 28 constructs a photoacoustic image of one frame based on the log-converted data of each line. The photoacoustic image construction means 28 constructs a photoacoustic image, for example, by converting the position of the photoacoustic signal (peak portion) in the time axis direction to the position in the depth direction of the photoacoustic image.

The observation method selection means 39 selects a display mode of the photoacoustic image. As for the display mode of the volume data of photoacoustic signal, for example, a three-dimensional image display mode, a tomographic image display mode, and a graphic display mode on a predetermined axis may be cited. Which display mode is to be used for the display is determined by initial setting or selected according to the user input via the input means 16.

The image combining means 38 generates volume data using the sequentially obtained photoacoustic signals. The generation of the volume data is performed by allocating the signal value of each photoacoustic signal in a virtual space according to the coordinates related to each photoacoustic image frame and pixel coordinates in the photoacoustic image. For example, the coordinate when the Qsw trigger signal is sent, the coordinate when the light is actually outputted, the coordinate when the sampling of the photoacoustic signal is started, and the like are related to each photoacoustic image frame. In allocating signal values, if positions where signal values are to be allocated overlap, for example, an average value or a maximum value of the signals is used as the signal value of the overlapped positions. Further, if no signal value to be allocated is present, an interpolation is preferably performed, as required, using signal values of adjacent positions. For example, the interpolation is performed by allocating a weighted average of four proximal points in order from the most proximal point to the interpolating position. This allows more natural form of volume data to be generated. The image combining means 38 further performs necessary processing (e.g., scale correction, coloring according to the voxel value, and the like) on the generated volume data.

Further, the image combining means 38 generates a photoacoustic image according to the observation method selected by the observation method selection means 39. The photoacoustic image generated according to the selected observation method is the final image to be displayed on the image display means 14 (display image). In the photoacoustic image generation method described above, it should be appreciated that, after a photoacoustic image is generated, the user may rotate or move the image, as required. That is, in the case where a three-dimensional image is displayed, if the user sequentially specifies or moves the direction of viewpoint using the input means 16, the photoacoustic image will be recalculated and the three-dimensional image will be rotated. The user may also change the observation method, as appropriate, using the input means 16.

The image display means 14 displays the display image generated by the image combining means 38.

As described above, also in the photoacoustic measurement apparatus according to the present embodiment, light (measuring light) is passed through the homogenizer once to flat-top the energy profile, and then the beam diameter of the laser light when entering the bundle fiber is controlled by the light condensing member. As a result of this, it is possible to transmit high energy light and eliminate imbalance in the amount of energy of light traveling through each of a plurality of optical fibers in photoacoustic measurements.

Then, as a result of this, stronger and homogenous photoacoustic signals may be obtained and high quality photoacoustic images may be generated. Further, the size and weight reduction of the transmission cable becomes possible, whereby the operability of the photoacoustic measurement apparatus is improved.

Second Embodiment of Photoacoustic Measurement Apparatus

Figure 22:
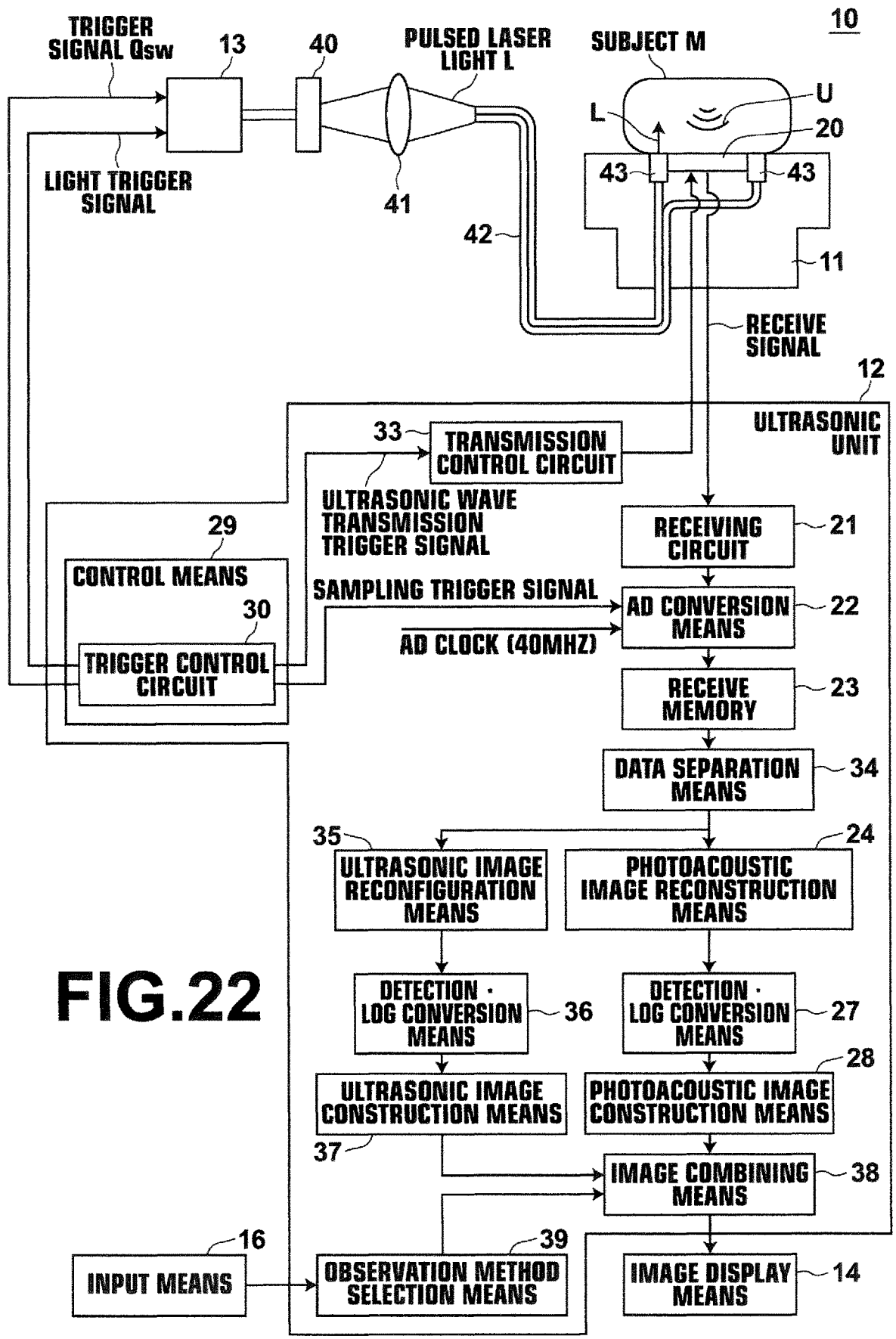
FIG. 22 is a schematic view illustrating a second embodiment of a photoacoustic image generation apparatus, as a photoacoustic measurement apparatus.

A second embodiment of photoacoustic measurement apparatus will be described next. Also in the present embodiment, a detailed description will be made of a case in which the photoacoustic measurement apparatus is a photoacoustic image generation apparatus. FIG. 22 is a block diagram of the photoacoustic image generation apparatus 10 of the present embodiment, illustrating the configuration thereof. The present embodiment differs from the first embodiment in that it generates an ultrasonic image in addition to the photoacoustic image. Therefore, the detailed description of the components identical to those of the first embodiment is omitted unless otherwise specifically required.

The photoacoustic image generation apparatus 10 of the present embodiment includes a probe 11 according to the present invention, an ultrasonic unit 12, a laser unit 13, an image display means 14, and an input means 16, as in the first embodiment.

<Ultrasonic Unit>

The ultrasonic unit 12 of the present embodiment further includes a transmission control circuit 33, a data separation means 34, an ultrasonic image reconstruction means 35, a detection·log conversion means 36, and an ultrasonic image construction means 37 in addition to the configuration of the photoacoustic image generation apparatus shown in FIG. 21. In the present embodiment, the receiving circuit 21, AD conversion means 22, receive memory 23, data separation means 34, ultrasonic image reconstruction means 24, detection·log conversion means 27, photoacoustic image construction means 28, ultrasonic image reconstruction means 35, detection·log conversion means 36, and ultrasonic image construction means 37 correspond, as a unit, to the acoustic image generation means of the present invention, as the signal processing means.

In the present embodiment, the probe 11 outputs (transmits) an ultrasonic wave to a subject and detects (receives) a reflected ultrasonic wave of a transmitted ultrasonic wave from the subject, in addition to the detection of a photoacoustic signal. As for the acoustic wave transducer that performs transmission and reception of ultrasonic waves, the acoustic wave transducer array 20 described above may be used or a new acoustic wave transducer array for transmission and reception of ultrasonic waves provided separately in the probe 11 may be used. Further, the transmission and reception of the ultrasonic wave may be separated. For example, an ultrasonic wave may be transmitted from a position different from the probe 11 and a reflected ultrasonic wave of the transmitted ultrasonic wave may be received by the probe 11.

The trigger control circuit 30 sends an ultrasonic wave transmission trigger signal that instructs transmission of an ultrasonic wave to the transmission control circuit 33 when generating an ultrasonic image. In response to the trigger signal, the transmission control circuit 33 causes an ultrasonic wave to be transmitted from the probe 11. After the transmission of the ultrasonic wave, the probe 11 detects a reflected ultrasonic wave from the subject.

The reflected ultrasonic wave detected by the probe 11 is inputted to the AD conversion means 22 via the receiving circuit 21. The trigger control circuit 30 sends a sampling trigger signal to the AD conversion means 22 in conjunction with the transmission timing of the ultrasonic wave to cause the sampling of the reflected ultrasonic wave to be started. Here, whereas the reflected ultrasonic wave reciprocates between the probe 11 and the ultrasonic wave reflection point, the photoacoustic signal travels one way from the point of generation to the probe 11. As the detection of reflected ultrasonic wave takes twice as long as the detection of a photoacoustic signal generated at the same depth, the sampling clock of the AD conversion means 22 may be reduced to half that of the photoacoustic signal sampling, for example, 20 MHz. The AD conversion means 22 stored a sampled signal of reflected ultrasonic wave in the receive memory 23. Either the sampling of photoacoustic signal or the sampling of reflected ultrasonic wave may precede the other.

The data separation means 34 separates the sampled signal of photoacoustic image from the sampled signal of reflected ultrasonic wave stored in the receive memory 23. The data separation means 34 inputs the separated sampled signal of photoacoustic image to the photoacoustic image reconstruction means 24. The generation of a photoacoustic image is performed in the same manner as in the first embodiment. In the meantime, the data separation means 34 inputs the separated sampled signal of reflected ultrasonic wave to the ultrasonic image reconstruction means 35.

The ultrasonic image reconstruction means 35 generates data of each line of an ultrasonic image based on the reflected ultrasonic waves (sampled signals thereof) detected by a plurality of acoustic wave transducers of the probe 11. For the generation of data of each line, the delay-and-sum method and the like may be used as in the generation of data of each line in the photoacoustic image reconstruction means 24. The detection·log conversion means 36 obtains an envelope of the data of each line outputted from the ultrasonic image reconstruction means 35 and performs log conversion on the obtained envelope.

The ultrasonic image construction means 37 generates an ultrasonic image based on the log-converted data of each line.

The image combining means 38 combines the photoacoustic image and the ultrasonic image. For example, the image combining means 38 combines the photoacoustic image and the ultrasonic image by superimposition. The combined image is displayed on the image display means 14. It is also possible to display the photoacoustic image and the ultrasonic image on the image display means side-by-side or by switching, without performing the image combining.

As described above, also in the photoacoustic measurement apparatus according to the present embodiment, light (measuring light) is passed through the homogenizer once to flat-top the energy profile, and then the beam diameter of the laser light when entering the bundle fiber is controlled by the light condensing member. This may provide advantageous effects identical to those of the first embodiment.

Further, the photoacoustic measurement apparatus of the present embodiment generates an ultrasonic image, in addition to a photoacoustic image. Therefore, a portion which cannot be imaged by the photoacoustic image may be observed by referring to the ultrasonic image.

In the foregoing, the description has been made of a case in which the photoacoustic measurement apparatus generates a photoacoustic image or an ultrasonic image. But the image generation is not necessarily required. For example, photoacoustic measurement apparatus may also be configured to measure the presence/absence or physical quantity of a measuring target based on the magnitude of photoacoustic signal.

What is claimed is:

1. A photoacoustic measuring apparatus, comprising:
a light source that emits measuring light;
an acoustic wave detecting probe that emits the measuring light towards a subject and detects photoacoustic waves which are generated within the subject due to the irradiation of the measuring light; and
an apparatus housing to which a base end of the probe is mounted; and
the probe having a holding section configured to hold a part of the probe, the holding section having a window at a portion at which the measuring light enters;
the apparatus housing having a mounting section which is detachably connected to the holding section;
a beam expander optical system that expands a beam diameter of the measuring light being mounted at the mounting section;
a light condensing member that condenses the measuring light transmitted through the beam expander optical system and a bundle fiber that includes a plurality of optical fibers that propagate the measuring light transmitted through the light condensing member being mounted to the holding section, the light condensing member being at least one of a mirror or a lens;
a homogenizer that flat tops an energy profile of the measuring light being mounted to the mounting section or the holding section;
the light condensing member condensing the measuring light such that a minimum beam diameter D of the measuring light defined by Formula 1 below satisfies Formula 2, which defines a relationship between the minimum beam diameter D and a diameter d of the bundle fiber; and
the bundle fiber being provided such that the measuring light enters therein in a state in which the beam diameter of the measuring light is 0.8 d or greater and 1.2 d or less:

$$D = 2.5 \cdot f \cdot \tan\left(\sqrt{\left(\frac{\phi}{2}\right)^2 + \left(\frac{\theta}{2}\right)^2}\right) \quad \text{Formula 1}$$

$$0.8d \leq D \leq 1.2d \quad \text{Formula 2}$$

wherein f is a focal length of the light condensing member, $\phi$ is a spreading angle of the measuring light when it enters the homogenizer, and $\theta$ is a diffusion angle of the homogenizer, and
the mounting section comprises a beam expander optical system immediately before an entrance side of the homogenizer, the beam expander optical system having an expansion factor that conforms to angular apertures of the plurality of optical fibers so that the high energy measuring light is expanded to the minimum beam diameter D that conforms to the angular apertures of the plurality of optical fibers; the minimum beam diameter D is set to inhibit damage to the bundle fiber and eliminate an imbalance in an amount of energy between each light traveling through each optical fiber of the bundle fiber.

2. A photoacoustic measuring apparatus as defined in claim 1, wherein:
the homogenizer is a light shaping diffuser in which small lenses are disposed randomly on one side of a substrate so that the measuring light is further diffused.

3. A photoacoustic measuring apparatus as defined in claim 1, wherein:
the holding section is configured to hold an entrance end portion of the optical fibers so as to cover an input surface of the bundle fiber.

4. A photoacoustic measuring apparatus as defined in claim 3, wherein:
the window is constituted by an ND filter.

5. A photoacoustic measuring apparatus as defined in claim 1, further comprising:
an aperture member having a taper structure and having an aperture that allows the measuring light, which is to enter the bundle fiber, to pass through and is provided at an entrance end of the bundle fiber, and gradually reduces the diameter of the aperture toward the entrance end to a size corresponding to the diameter of the bundle fiber.

6. A photoacoustic measuring apparatus as defined in any one of claim 1, wherein:
the holding section includes therein a light guide member formed of a cap and a ring shaped chip made of a material resistant to optical energy and fitted around the cap.

7. A photoacoustic measuring apparatus as defined in claim 1, wherein:
the holding section includes therein a light guide member having an aperture stop and a relay lens system.

8. A photoacoustic measuring apparatus as defined in claim 1, wherein:
an entrance end of the bundle fiber is fusion processed.

9. A photoacoustic measuring apparatus as defined in claim 1, wherein:
the outer circumferences of the plurality of optical fibers are covered with a material having high durability against optical energy at an entrance end of the optical fibers.

10. A photoacoustic measuring apparatus as defined in claim 9, wherein:
the material having high durability against optical energy is silica.

11. A photoacoustic measuring apparatus as defined in claim 1, further comprising:
at least one light guide plate having a connection surface to which at least some of exit ends of the plurality of optical fibers are connected and an exit surface from which the measuring light that enters from the connection surface exits.

12. A photoacoustic measuring apparatus as defined in claim 11, wherein:
a plurality of light guide plates are disposed across an acoustic wave transducer.

13. A photoacoustic measuring apparatus as defined in claim 1, further comprising:
a signal processor that processes photoacoustic signals of the photoacoustic waves detected by an acoustic wave transducer.

14. A photoacoustic measuring apparatus as defined in claim 13, wherein:

the signal processor comprises an acoustic image generator that generates photoacoustic images based on the photoacoustic signals.

15. A photoacoustic measuring apparatus as defined in claim 14, wherein:
the acoustic wave transducer detects reflected acoustic waves of acoustic waves which are transmitted toward the subject; and
the acoustic image generator generates reflected acoustic wave images based on signals of the reflected acoustic waves.

\* \* \* \* \*